United States Patent
Luo (10) Patent No.: US 9,403,919 B2
(45) Date of Patent: Aug. 2, 2016

(54) POLYMERS FUNCTIONALIZED WITH A CARBOXYLIC OR THIOCARBOXYLIC ESTER CONTAINING A SILYLATED AMINO GROUP

(75) Inventor: Steven Luo, Copley, OH (US)

(73) Assignee: Bridgestone Corporation, Tokyo (JP)

( * ) Notice: Subject to any disclaimer, the term of this patent is extended or adjusted under 35 U.S.C. 154(b) by 0 days.

(21) Appl. No.: 14/008,925

(22) PCT Filed: Mar. 29, 2012

(86) PCT No.: PCT/US2012/031139
§ 371 (c)(1),
(2), (4) Date: Sep. 30, 2013

(87) PCT Pub. No.: WO2012/135451
PCT Pub. Date: Oct. 4, 2012

(65) Prior Publication Data
US 2014/0018500 A1    Jan. 16, 2014

Related U.S. Application Data

(60) Provisional application No. 61/468,888, filed on Mar. 29, 2011.

(51) Int. Cl.
| | |
|---|---|
| *C08C 19/25* | (2006.01) |
| *C08F 8/10* | (2006.01) |
| *C08C 19/44* | (2006.01) |
| *C07F 7/10* | (2006.01) |
| *C08F 236/10* | (2006.01) |
| *C08K 5/544* | (2006.01) |

(52) U.S. Cl.
CPC . *C08C 19/25* (2013.01); *C07F 7/10* (2013.01); *C08C 19/44* (2013.01); *C08F 8/10* (2013.01); *C08F 236/10* (2013.01); *C08K 5/544* (2013.01)

(58) Field of Classification Search
None
See application file for complete search history.

(56) References Cited

U.S. PATENT DOCUMENTS

| | | |
|---|---|---|
| 3,426,006 A | 2/1969 | Nutzel et al. |
| 3,652,516 A | 3/1972 | Farrar |
| 3,842,111 A | 10/1974 | Meyer et al. |
| 3,873,489 A | 3/1975 | Thurn et al. |
| 3,978,103 A | 8/1976 | Meyer-Simon et al. |
| 3,997,581 A | 12/1976 | Pletka et al. |
| 4,002,594 A | 1/1977 | Fetterman |
| 4,429,091 A | 1/1984 | Hall |
| 4,906,706 A | 3/1990 | Hattori et al. |
| 4,990,573 A | 2/1991 | Andreussi et al. |
| 5,064,910 A | 11/1991 | Hattori et al. |
| 5,227,425 A | 7/1993 | Rauline |
| 5,268,439 A | 12/1993 | Hergenrother et al. |
| 5,329,005 A | 7/1994 | Lawson et al. |
| 5,332,810 A | 7/1994 | Lawson et al. |
| 5,393,721 A | 2/1995 | Kitamura et al. |
| 5,491,230 A | 2/1996 | Lawson et al. |
| 5,496,940 A | 3/1996 | Lawson et al. |
| 5,521,309 A | 5/1996 | Antkowiak et al. |
| 5,552,483 A | 9/1996 | Hergenrother et al. |
| 5,567,784 A | 10/1996 | Wieder et al. |
| 5,574,109 A | 11/1996 | Lawson et al. |
| 5,578,542 A | 11/1996 | Lawson et al. |
| 5,580,919 A | 12/1996 | Agostini et al. |
| 5,583,245 A | 12/1996 | Parker et al. |
| 5,663,396 A | 9/1997 | Musleve et al. |
| 5,674,932 A | 10/1997 | Agostini et al. |
| 5,684,171 A | 11/1997 | Wideman et al. |
| 5,684,172 A | 11/1997 | Wideman et al. |
| 5,696,197 A | 12/1997 | Smith et al. |
| 5,698,646 A | 12/1997 | Kitamura et al. |
| 5,717,022 A | 2/1998 | Beckmann et al. |
| 5,719,207 A | 2/1998 | Cohen et al. |
| 5,786,441 A | 7/1998 | Lawson et al. |
| 5,844,050 A | 12/1998 | Fukahori et al. |
| 5,866,171 A | 2/1999 | Kata |
| 5,876,527 A | 3/1999 | Tsuruta et al. |
| 5,931,211 A | 8/1999 | Tamura |
| 5,971,046 A | 10/1999 | Koch et al. |
| 6,342,552 B1 | 1/2002 | Hergenrother et al. |
| 6,525,118 B2 | 2/2003 | Hergenrother et al. |
| 6,579,949 B1 | 6/2003 | Hergenrother et al. |
| 6,590,017 B1 | 7/2003 | Hergenrother et al. |
| 6,608,145 B1 | 8/2003 | Lin et al. |

(Continued)

FOREIGN PATENT DOCUMENTS

| | | |
|---|---|---|
| EP | 0890606 A1 | 1/1999 |
| EP | 1457501 A1 | 9/2004 |

(Continued)

OTHER PUBLICATIONS

Jagur-Grodzinski, Joseph, "Functional polymers by living anionic polymerization," Journal of Polymer Science Part A: Polymer Chemistry, vol. 40, Issue 13, pp. 2116-2133 (Jul. 1, 2002).

(Continued)

*Primary Examiner* — Marc Zimmer
(74) *Attorney, Agent, or Firm* — Meredith E. Hooker; Arthur M. Reginelli (57) ABSTRACT

A method for preparing a functionalized polymer, the method comprising the steps of: (i) polymerizing monomer with an anionic initiator to form a reactive polymer; and (ii) reacting the reactive polymer with a carboxylic or thiocarboxylic ester containing a silylated amino group, where the silylated amino group is directly attached to a moiety selected from the group consisting of acyclic moieties, heterocyclic moieties, and nonaromatic cyclic moieties.

13 Claims, 1 Drawing Sheet

(56) References Cited

U.S. PATENT DOCUMENTS

| | | |
|---|---|---|
| 6,667,362 B2 | 12/2003 | Robert et al. |
| 6,683,135 B2 | 1/2004 | Cruse et al. |
| 6,838,526 B1 | 1/2005 | Sone et al. |
| 6,977,281 B1 | 12/2005 | Ozawa et al. |
| 6,992,147 B1 | 1/2006 | Ozawa et al. |
| 7,351,776 B2 | 4/2008 | Tartamella et al. |
| 2004/0147694 A1 | 7/2004 | Sone et al. |
| 2006/0004131 A1 | 1/2006 | Ozawa et al. |
| 2006/0025539 A1 | 2/2006 | Ozawa et al. |
| 2006/0030657 A1 | 2/2006 | Hogan et al. |
| 2006/0030677 A1 | 2/2006 | Ozawa et al. |
| 2006/0241241 A1 | 10/2006 | Yan et al. |
| 2006/0264589 A1 | 11/2006 | Yan |
| 2006/0264590 A1 | 11/2006 | Hogan et al. |
| 2010/0267918 A1 | 10/2010 | Kura et al. |
| 2010/0317818 A1 | 12/2010 | Hogan et al. |

FOREIGN PATENT DOCUMENTS

| | | |
|---|---|---|
| JP | 58-136623 A | 8/1983 |
| JP | S62-101640 A | 5/1987 |
| WO | 9323453 A1 | 11/1993 |
| WO | WO 2009/086477 * | 7/2009 |

OTHER PUBLICATIONS

Young, Jung Doo, International Search Report with Written Opinion from PCT Application No. PCT/US2012/031139, 8 pp. (Oct. 23, 2012).

Giani, Elena, Supplementary European Search Report from European Patent Application No. 12765972.0, 5 pp. (Jan. 5, 2015).

* cited by examiner

POLYMERS FUNCTIONALIZED WITH A CARBOXYLIC OR THIOCARBOXYLIC ESTER CONTAINING A SILYLATED AMINO GROUP

FIELD OF THE INVENTION

One or more embodiments of the present invention relate to functionalized polymers and methods for their manufacture.

BACKGROUND OF THE INVENTION

In the art of manufacturing tires, it is desirable to employ rubber vulcanizates that demonstrate reduced hysteresis, i.e., less loss of mechanical energy to heat. For example, rubber vulcanizates that show reduced hysteresis are advantageously employed in tire components, such as sidewalls and treads, to yield tires having desirably low rolling resistance. The hysteresis of a rubber vulcanizate is often attributed to the free polymer chain ends within the crosslinked rubber network, as well as the dissociation of filler agglomerates.

Functionalized polymers have been employed to reduce the hysteresis of rubber vulcanizates. The functional group of the functionalized polymer may reduce the number of free polymer chain ends via interaction with filler particles. Also, the functional group may reduce filler agglomeration. Nevertheless, whether a particular functional group imparted to a polymer can reduce hysteresis is often unpredictable.

Functionalized polymers may be prepared by post-polymerization treatment of reactive polymers with certain functionalizing agents. However, whether a reactive polymer can be functionalized by treatment with a particular functionalizing agent can be unpredictable. For example, functionalizing agents that work for one type of polymer do not necessarily work for another type of polymer, and vice versa.

Anionic initiators are known to be useful for the polymerization of conjugated diene monomers to form polydienes having a combination of 1,2-, cis-1,4- and trans-1,4-linkages. Anionic initiators are also useful for the copolymerization of conjugated diene monomers with vinyl-substituted aromatic compounds. The polymers prepared with anionic initiators may display living characteristics in that, upon completion of the polymerization, the polymer chains possess living ends that are capable of reacting with additional monomers for further chain growth or reacting with certain functionalizing agents to give functionalized polymers.

Because functionalized polymers are advantageous, especially in the manufacture of tires, there exists a need to develop new functionalized polymers that give reduced hysteresis.

SUMMARY OF THE INVENTION

Embodiments of the present invention provide a method for preparing a functionalized polymer, the method comprising the steps of: (i) polymerizing monomer with an anionic initiator to form a reactive polymer; and (ii) reacting the reactive polymer with a carboxylic or thiocarboxylic ester containing a silylated amino group, where the silylated amino group is directly attached to a moiety selected from the group consisting of acyclic moieties, heterocyclic moieties, and non-aromatic cyclic moieties.

Embodiments of the present invention further provide a method for preparing a functionalized polymer, the method comprising the steps of: (i) polymerizing monomer with an anionic initiator to form a reactive polymer; and (ii) reacting the reactive polymer with a carboxylic or thiocarboxylic ester containing a silylated amino group defined by the formula I:

where $R^1$ is a monovalent organic group, $R^2$ is a divalent organic group, $R^3$ is a hydrocarbyl group, each $R^4$ is independently a hydrogen atom or a monovalent organic group, or $R^3$ joins with an $R^4$ to form a hydrocarbylene group, and each $\alpha$ is independently an oxygen atom or a sulfur atom, with the proviso that $R^2$ is an acyclic divalent organic group, a heterocyclic divalent organic group, a non-aromatic cyclic divalent organic group that is devoid of heteroatoms, or a divalent organic group containing an aromatic ring that is devoid of heteroatoms so long as, where $R^2$ is a divalent organic group containing an aromatic ring that is devoid of heteroatoms, the silylated amino group is not directly attached to the aromatic ring; or by the formula II:

where $R^1$ is a monovalent organic group, $R^2$ is a divalent organic group, each $R^4$ is independently a hydrogen atom or a monovalent organic group, or two $R^4$ groups join to form a divalent organic group, and each $\alpha$ is independently an oxygen atom or a sulfur atom, with the proviso that $R^2$ is an acyclic divalent organic group, a heterocyclic divalent organic group, a non-aromatic cyclic divalent organic group that is devoid of heteroatoms, or a divalent organic group containing an aromatic ring that is devoid of heteroatoms so long as, where $R^2$ is a divalent organic group containing an aromatic ring that is devoid of heteroatoms, the silylated amino group is not directly attached to the aromatic ring.

DETAILED DESCRIPTION OF ILLUSTRATIVE EMBODIMENTS

According to one or more embodiments of the present invention, a reactive polymer is prepared by anionically polymerizing conjugated diene monomer and optionally monomer copolymerizable therewith, and this reactive polymer is then functionalized by reaction with a carboxylic or thiocarboxylic ester containing a silylated amino group. The resultant functionalized polymers can be used in the manufacture of tire components. In one or more embodiments, the resultant functionalized polymers provide tire components that exhibit advantageously low hysteresis.

Examples of conjugated diene monomer include 1,3-butadiene, isoprene, 1,3-pentadiene, 1,3-hexadiene, 2,3-dimethyl-1,3-butadiene, 2-ethyl-1,3-butadiene, 2-methyl-1,3-pentadiene, 3-methyl-1,3-pentadiene, 4-methyl-1,3-pentadiene, and 2,4-hexadiene. Mixtures of two or more conjugated dienes may also be utilized in copolymerization.

Examples of monomer copolymerizable with conjugated diene monomer include vinyl-substituted aromatic compounds such as styrene, p-methylstyrene, α-methylstyrene, and vinylnaphthalene.

In accordance with the present invention, a reactive polymer is prepared by anionic polymerization, wherein monomer is polymerized by using an anionic initiator. The key mechanistic features of anionic polymerization have been described in books (e.g., Hsieh, H. L.; Quirk, R. P. Anionic Polymerization: Principles and Practical Applications; Marcel Dekker New York, 1996) and review articles (e.g., Hadjichristidis, N.; Pitsikalis, M.; Pispas, S.; Iatrou, H.; Chem. Rev. 2001, 101 (12), 3747-3792). Anionic initiators may advantageously produce living polymers that, prior to quenching, are capable of reacting with additional monomers for further chain growth or reacting with certain functionalizing agents to give functionalized polymers.

The practice of this invention is not limited by the selection of any particular anionic initiators. In one or more embodiments, the anionic initiator employed is a functional initiator that imparts a functional group at the head of the polymer chain (i.e., the location from which the polymer chain is started). In particular embodiments, the functional group includes one or more heteroatoms (e.g., nitrogen, oxygen, boron, silicon, sulfur, tin, and phosphorus atoms) or heterocyclic groups. In certain embodiments, the functional group reduces the 50° C. hysteresis loss of carbon-black filled vulcanizates prepared from polymers containing the functional group as compared to similar carbon-black filled vulcanizates prepared from polymer that does not include the functional group.

Exemplary anionic initiators include organolithium compounds. In one or more embodiments, organolithium compounds may include heteroatoms. In these or other embodiments, organolithium compounds may include one or more heterocyclic groups. Types of organolithium compounds include alkyllithium, aryllithium compounds, and cycloalkyllithium compounds. Specific examples of organolithium compounds include ethyllithium, n-propyllithium, isopropyllithium, n-butyllithium, sec-butyllithium, t-butyllithium, n-amyllithium, isoamyllithium, and phenyllithium.

In particular embodiments, the organolithium compounds include a cyclic amine-containing compound such as lithiohexamethyleneimine. These and related useful initiators are disclosed in the U.S. Pat. Nos. 5,332,810, 5,329,005, 5,578, 542, 5,393,721, 5,698,646, 5,491,230, 5,521,309, 5,496,940, 5,574,109, and 5,786,441, which are incorporated herein by reference. In other embodiments, the organolithium compounds include lithiated alkylthioacetals such as 2-lithio-2-methyl-1,3-dithiane. These and related useful initiators are disclosed in U.S. Publ. Nos. 2006/0030657, 2006/0264590, and 2006/0264589, which are incorporated herein by reference. In still other embodiments, the organolithium compounds include alkoxysilyl-containing initiators, such as lithiated t-butyldimethylpropoxysilane. These and related useful initiators are disclosed in U.S. Publ. No. 2006/0241241, which is incorporated herein by reference.

Other anionic initiators include organosodium compounds such as phenylsodium and 2,4,6-trimethylphenylsodium. Also contemplated are those anionic initiators that give rise to di-living polymers, wherein both ends of a polymer chain are living. Examples of such initiators include dilithio initiators such as those prepared by reacting 1,3-diisopropenylbenzene with sec-butyllithium. These and related difunctional initiators are disclosed in U.S. Pat. No. 3,652,516, which is incorporated herein by reference. Radical anionic initiators may also be employed, including those described in U.S. Pat. No. 5,552,483, which is incorporated herein by reference.

In one or more embodiments, the anionic initiator employed is trialkyltinlithium compound such as tri-n-butyltinlithium. These and related useful initiators are disclosed in U.S. Pat. Nos. 3,426,006 and 5,268,439, which are incorporated herein by reference.

When elastomeric copolymers containing conjugated diene monomers and vinyl-substituted aromatic monomers are prepared by anionic polymerization, the conjugated diene monomers and vinyl-substituted aromatic monomers may be used at a weight ratio of 95:5 to 50:50, or in other embodiments, 90:10 to 65:35. In order to promote the randomization of comonomers in copolymerization and to control the microstructure (such as 1,2-linkage of conjugated diene monomer) of the polymer, a randomizer, which is typically a polar coordinator, may be employed along with the anionic initiator.

Compounds useful as randomizers include those having an oxygen or nitrogen heteroatom and a non-bonded pair of electrons. Exemplary types of randomizers include linear and cyclic oligomeric oxolanyl alkanes; dialkyl ethers of mono and oligo alkylene glycols (also known as glyme ethers); crown ethers; tertiary amines; linear THF oligomers; alkali metal alkoxides; and alkali metal sulfonates. Linear and cyclic oligomeric oxolanyl alkanes are described in U.S. Pat. No. 4,429,091, which is incorporated herein by reference. Specific examples of randomizers include 2,2-bis(2'-tetrahydrofuryl)propane, 1,2-dimethoxyethane, N,N,N',N'-tetramethylethylenediamine (TMEDA), tetrahydrofuran (THF), 1,2-dipiperidylethane, dipiperidylmethane, hexamethylphosphoramide, N,N'-dimethylpiperazine, diazabicyclooctane, dimethyl ether, diethyl ether, tri-n-butylamine, potassium t-amylate, potassium 4-dodecylsulfonate, and mixtures thereof.

The amount of randomizer to be employed may depend on various factors such as the desired microstructure of the polymer, the ratio of monomer to comonomer, the polymerization temperature, as well as the nature of the specific randomizer and initiator employed. In one or more embodiments, the amount of randomizer employed may range between 0.05 and 100 moles per mole of the anionic initiator.

The anionic initiator and the randomizer can be introduced to the polymerization system by various methods. In one or more embodiments, the anionic initiator and the randomizer may be added separately to the monomer to be polymerized in either a stepwise or simultaneous manner. In other embodiments, the anionic initiator and the randomizer may be premixed outside the polymerization system either in the absence of any monomer or in the presence of a small amount of monomer, and the resulting mixture may be aged, if desired, and then added to the monomer that is to be polymerized.

In one or more embodiments, regardless of what type of anionic initiator is used to prepare the reactive polymer, a solvent may be employed as a carrier to either dissolve or suspend the initiator in order to facilitate the delivery of the initiator to the polymerization system. In other embodiments, monomer can be used as the carrier. In yet other embodiments, the initiator can be used in their neat state without any solvent.

In one or more embodiments, suitable solvents include those organic compounds that will not undergo polymerization or incorporation into propagating polymer chains during the polymerization of monomer in the presence of the initiator. In one or more embodiments, these organic species are liquid at ambient temperature and pressure. In one or more embodiments, these organic solvents are inert to the initiator. Exemplary organic solvents include hydrocarbons with a low or relatively low boiling point such as aromatic hydrocarbons, aliphatic hydrocarbons, and cycloaliphatic hydrocarbons. Non-limiting examples of aromatic hydrocarbons include benzene, toluene, xylenes, ethylbenzene, diethylbenzene, and mesitylene. Non-limiting examples of aliphatic hydrocarbons include n-pentane, n-hexane, n-heptane, n-octane, n-nonane, n-decane, isopentane, isohexanes, isopentanes, isooctanes, 2,2-dimethylbutane, petroleum ether, kerosene, and petroleum spirits. And, non-limiting examples of cycloaliphatic hydrocarbons include cyclopentane, cyclohexane, methylcyclopentane, and methylcyclohexane. Mixtures of the above hydrocarbons may also be used. As is known in the art, aliphatic and cycloaliphatic hydrocarbons may be desirably employed for environmental reasons. The low-boiling hydrocarbon solvents are typically separated from the polymer upon completion of the polymerization.

Other examples of organic solvents include high-boiling hydrocarbons of high molecular weights, including hydrocarbon oils that are commonly used to oil-extend polymers. Examples of these oils include paraffinic oils, aromatic oils, naphthenic oils, vegetable oils other than castor oils, and low PCA oils including MES, TDAE, SRAE, heavy naphthenic oils. Since these hydrocarbons are non-volatile, they typically do not require separation and remain incorporated in the polymer.

The production of the reactive polymer according to this invention can be accomplished by polymerizing conjugated diene monomer, optionally together with monomer copolymerizable with conjugated diene monomer, in the presence of a catalytically effective amount of an anionic initiator. The introduction of the initiator, the conjugated diene monomer, optionally the comonomer, and any solvent, if employed, forms a polymerization mixture in which the reactive polymer is formed. The amount of the initiator to be employed may depend on the interplay of various factors such as the type of initiator employed, the purity of the ingredients, the polymerization temperature, the polymerization rate and conversion desired, the molecular weight desired, and many other factors. Accordingly, a specific initiator amount cannot be definitively set forth except to say that catalytically effective amounts of the initiator may be used.

In one or more embodiments, the initiator loading (e.g., an alkyllithium compound) may be varied from about 0.05 to about 100 mmol, in other embodiments from about 0.1 to about 50 mmol, and in still other embodiments from about 0.2 to about 5 mmol per 100 gram of monomer.

In one or more embodiments, the polymerization may be carried out in a polymerization system that includes a substantial amount of solvent. In one embodiment, a solution polymerization system may be employed in which both the monomer to be polymerized and the polymer formed are soluble in the solvent. In another embodiment, a precipitation polymerization system may be employed by choosing a solvent in which the polymer formed is insoluble. In both cases, an amount of solvent in addition to the amount of solvent that may be used in preparing the initiator is usually added to the polymerization system. The additional solvent may be the same as or different from the solvent used in preparing the initiator. Exemplary solvents have been set forth above. In one or more embodiments, the solvent content of the polymerization mixture may be more than 20% by weight, in other embodiments more than 50% by weight, and in still other embodiments more than 80% by weight based on the total weight of the polymerization mixture.

In other embodiments, the polymerization system employed may be generally considered a bulk polymerization system that includes substantially no solvent or a minimal amount of solvent. Those skilled in the art will appreciate the benefits of bulk polymerization processes (i.e., processes where monomer acts as the solvent), and therefore the polymerization system includes less solvent than will deleteriously impact the benefits sought by conducting bulk polymerization. In one or more embodiments, the solvent content of the polymerization mixture may be less than about 20% by weight, in other embodiments less than about 10% by weight, and in still other embodiments less than about 5% by weight based on the total weight of the polymerization mixture. In another embodiment, the polymerization mixture contains no solvents other than those that are inherent to the raw materials employed. In still another embodiment, the polymerization mixture is substantially devoid of solvent, which refers to the absence of that amount of solvent that would otherwise have an appreciable impact on the polymerization process. Polymerization systems that are substantially devoid of solvent may be referred to as including substantially no solvent. In particular embodiments, the polymerization mixture is devoid of solvent.

The polymerization may be conducted in any conventional polymerization vessels known in the art. In one or more embodiments, solution polymerization can be conducted in a conventional stirred-tank reactor. In other embodiments, bulk polymerization can be conducted in a conventional stirred-tank reactor, especially if the monomer conversion is less than about 60%. In still other embodiments, especially where the monomer conversion in a bulk polymerization process is higher than about 60%, which typically results in a highly viscous cement, the bulk polymerization may be conducted in an elongated reactor in which the viscous cement under polymerization is driven to move by piston, or substantially by piston. For example, extruders in which the cement is pushed along by a self-cleaning single-screw or double-screw agitator are suitable for this purpose. Examples of useful bulk polymerization processes are disclosed in U.S. Pat. No. 7,351,776, which is incorporated herein by reference.

In one or more embodiments, all of the ingredients used for the polymerization can be combined within a single vessel (e.g., a conventional stirred-tank reactor), and all steps of the polymerization process can be conducted within this vessel. In other embodiments, two or more of the ingredients can be pre-combined in one vessel and then transferred to another vessel where the polymerization of monomer (or at least a major portion thereof) may be conducted.

The polymerization can be carried out as a batch process, a continuous process, or a semi-continuous process. In the semi-continuous process, the monomer is intermittently charged as needed to replace that monomer already polymerized. In one or more embodiments, the conditions under which the polymerization proceeds may be controlled to maintain the temperature of the polymerization mixture within a range from about −10° C. to about 200° C., in other embodiments from about 0° C. to about 150° C., and in other embodiments from about 20° C. to about 100° C. In one or more embodiments, the heat of polymerization may be removed by external cooling by a thermally controlled reactor jacket, internal cooling by evaporation and condensation of the monomer through the use of a reflux condenser connected to the reactor, or a combination of the two methods. Also, the polymerization conditions may be controlled to conduct the polymerization under a pressure of from about 0.1 atmosphere to about 50 atmospheres, in other embodiments from about 0.5 atmosphere to about 20 atmosphere, and in other embodiments from about 1 atmosphere to about 10 atmospheres. In one or more embodiments, the pressures at which the polymerization may be carried out include those that ensure that the majority of the monomer is in the liquid phase. In these or other embodiments, the polymerization mixture may be maintained under anaerobic conditions.

Some or all of the polymer chains in the resulting reactive polymer may possess reactive chain ends before the polymerization mixture is quenched. Thus, reference to a reactive polymer refers to a polymer having a reactive chain end deriving from a synthesis of the polymer by using an anionic initiator. As noted above, the reactive polymer prepared with an anionic initiator (e.g., an alkyllithium initiator) may be referred to as a living polymer. In one or more embodiments, a polymerization mixture including the reactive polymer may be referred to as an active polymerization mixture. The percentage of polymer chains possessing a reactive end depends on various factors such as the type of initiator, the type of monomer, the purity of the ingredients, the polymerization temperature, the monomer conversion, and many other factors. In one or more embodiments, at least about 20% of the polymer chains possess a reactive end, in other embodiments at least about 50% of the polymer chains possess a reactive end, and in still other embodiments at least about 80% of the polymer chains possess a reactive end. In any event, the reactive polymer can be reacted with a carboxylic or thiocarboxylic ester containing a silylated amino group to form the functionalized polymer of this invention.

In one or more embodiments, carboxylic or thiocarboxylic esters containing a silylated amino group include those compounds that contain one or more carboxylic or thiocarboxylic ester groups and one or more silylated amino groups. For purposes of this specification, and for ease of explanation, the carboxylic or thiocarboxylic esters containing a silylated amino group may be simply referred to as the esters.

In one or more embodiments, carboxylic or thiocarboxylic ester groups may be defined by the formula where $R^1$ is a monovalent organic group and each α is independently an oxygen atom or a sulfur atom. As will be described below, the monovalent organic group $R^1$ may be a hydrocarbyl or silyl group. As those skilled in the art appreciate, where both α atoms are oxygen atoms, the ester group may be referred to as a carboxylic ester group. Where one or both α atoms are sulfur atoms, the ester group may be referred to as a thiocarboxylic ester group. More specifically, where one α atom is a sulfur atom (either α atom) and the other α atom is an oxygen atom, the ester group may be referred to as a monothiocarboxylic ester group, and the corresponding ester may be referred to as a monothiocarboxylic ester. Where both α atoms are sulfur atoms, the ester group may be referred to as a dithiocarboxylic ester group, and the corresponding ester may be referred to as a dithiocarboxylic ester. For purposes of this specification, reference to a thiocarboxylic ester group may encompass both monothiocarboxylic ester groups and dithiocarboxylic ester groups, and, correspondingly, reference to a thiocarboxylic ester may encompass both monothiocarboxylic esters and dithiocarboxylic esters.

In one or more embodiments, silylated amino groups include those amino groups that are formed or derived by replacing one hydrogen atom of the parent amino group (i.e. —$NH_2$) with a silyl group and replacing the other hydrogen atom of the parent amino group with a hydrocarbyl or silyl group. Where the silylated amino group includes a silyl group and a hydrocarbyl group, the group may be referred to as a monosilylated amino group. Where the silylated amino group includes two silyl groups, the group may be referred to as a disilylated amino group.

Exemplary types of silylated amino groups include, but are not limited to, bis(trihydrocarbylsilyl)amino, bis(dihydrocarbylhydrosilyl)amino, 1-aza-disila-1-cyclohydrocarbyl, (trihydrocarbylsilyl)(hydrocarbyl)amino, (dihydrocarbylhydrosilyl)(hydrocarbyl)amino, and 1-aza-2-sila-1-cyclohydrocarbyl groups.

Specific examples of bis(trihydrocarbylsilyl)amino groups include, but are not limited to, bis(trimethylsilyl)amino, bis(triethylsilyl)amino, bis(triisopropylsilyl)amino, bis(tri-n-propylsilyl)amino, bis(triisobutylsilyl)amino, bis(tri-t-butylsilyl)amino, and bis(triphenylsilyl)amino groups.

Specific examples of bis(dihydrocarbylhydrosilyl)amino groups include, but are not limited to, bis(dimethylhydrosilyl)amino, bis(diethylhydrosilyl)amino, bis(diisopropylhydrosilyl)amino, bis(di-n-propylhydrosilyl)amino, bis(diisobutylhydrosilyl)amino, bis(di-t-butylhydrosilyl)amino, and bis(diphenylhydrosilyl)amino groups.

Specific examples of 1-aza-disila-1-cyclohydrocarbyl groups include, but are not limited to, 2,2,5,5-tetramethyl-1-aza-2,5-disila-1-cyclopentyl, 2,2,5,5-tetraethyl-1-aza-2,5-disila-1-cyclopentyl, 2,2,5,5-tetraphenyl-1-aza-2,5-disila-1-cyclopentyl, 2,2,6,6-tetramethyl-1-aza-2,6-disila-1-cyclohexyl, 2,2,6,6-tetraethyl-1-aza-2,6-disila-1-cyclohexyl, and 2,2,6,6-tetraphenyl-1-aza-2,6-disila-1-cyclohexyl groups.

Specific examples of (trihydrocarbylsilyl)(hydrocarbyl)amino groups include, but are not limited to, (trimethylsilyl)(methyl)amino, (triethylsilyl)(methyl)amino, (triphenylsilyl)(methyl)amino, (trimethylsilyl)(ethyl)amino, (triethylsilyl)(phenyl)amino, and (triisopropylsilyl)(methyl)amino groups.

Specific examples of (dihydrocarbylhydrosilyl)(hydrocarbyl)amino groups include, but are not limited to, (dimethylhydrosilyl)(methyl)amino, (diethylhydrosilyl)(methyl)amino, (diisopropylhydrosilyl)(methyl)amino, (di-n-propylhydrosilyl)(ethyl)amino, (diisobutylhydrosilyl)(phenyl)amino, (di-t-butylhydrosilyl)(phenyl)amino, and (diphenylhydrosilyl)(phenyl)amino groups.

Specific examples of 1-aza-2-sila-1-cyclohydrocarbyl groups include, but are not limited to, 2,2-dimethyl-1-aza-2-sila-1-cyclopentyl, 2,2-diethyl-1-aza-2-sila-1-cyclopentyl, 2,2-diphenyl-1-aza-2-sila-1-cyclopentyl, 2,2-diisopropyl-1-aza-2-sila-1-cyclohexyl, 2,2-dibutyl-1-aza-2-sila-1-cyclohexyl, and 2,2-diphenyl-1-aza-2-sila-1-cyclohexyl groups.

In particular embodiments, the carboxylic or thiocarboxylic esters containing a silylated amino group include those compounds where the silylated amino group is directly attached to an acyclic moiety. In other particular embodiments, the carboxylic or thiocarboxylic esters containing a silylated amino group include those compounds where the carboxylic or thiocarboxylic ester group is directly attached to an acyclic moiety. In yet other particular embodiments, the carboxylic or thiocarboxylic esters containing a silylated amino group include those compounds where both the silylated amino group and the carboxylic or thiocarboxylic ester group are directly attached to an acyclic moiety.

In particular embodiments, the carboxylic or thiocarboxylic esters containing a silylated amino group include those compounds where the silylated amino group is directly attached to a heterocyclic moiety. In other particular embodiments, the carboxylic or thiocarboxylic esters containing a silylated amino group include those compounds where the carboxylic or thiocarboxylic ester group is directly attached to a heterocyclic moiety. In yet other particular embodiments, the carboxylic or thiocarboxylic esters containing a silylated amino group include those compounds where both the silylated amino group and the carboxylic or thiocarboxylic ester group are directly attached to a heterocyclic moiety.

In particular embodiments, the carboxylic or thiocarboxylic esters containing a silylated amino group include those compounds where the silylated amino group is directly attached to a non-aromatic cyclic moiety. In other particular embodiments, the carboxylic or thiocarboxylic esters containing a silylated amino group include those compounds where the carboxylic or thiocarboxylic ester group is directly attached to a non-aromatic cyclic moiety. In yet other particular embodiments, the carboxylic or thiocarboxylic esters containing a silylated amino group include those compounds where both the silylated amino group and the carboxylic or thiocarboxylic ester group are directly attached to a non-aromatic cyclic moiety.

In particular embodiments, the carboxylic or thiocarboxylic esters containing a silylated amino group include those compounds where the carboxylic or thiocarboxylic ester group is directly attached to an aromatic moiety (e.g., a phenyl ring) that is devoid of heteroatoms and the silylated amino group is directly attached to an acyclic moiety, a heterocyclic moiety, or a non-aromatic cyclic moiety.

In one or more embodiments, this invention specifically excludes those compounds where the silylated amino group, in other embodiments where the carboxylic or thiocarboxylic ester group, or in other embodiments where both the silylated amino group and the carboxylic or thiocarboxylic ester group are directly attached to an aromatic moiety (e.g., a phenyl ring) that is devoid of heteroatoms.

In one or more embodiments, carboxylic or thiocarboxylic esters containing a monosilylated amino group may be defined by the formula I:

where $R^1$ is a monovalent organic group, $R^2$ is a divalent organic group, $R^3$ is a hydrocarbyl group, each $R^4$ is independently a hydrogen atom or a monovalent organic group, or $R^3$ joins with an $R^4$ to form a hydrocarbylene group, and each $\alpha$ is independently an oxygen atom or a sulfur atom. In one or more embodiments, the divalent organic group $R^2$ may contain one or more additional silylated amino groups and/or one or more additional carboxylic or thiocarboxylic ester groups.

In one or more embodiments, carboxylic or thiocarboxylic esters containing a disilylated amino group may be represented by the formula II:

where $R^1$ is a monovalent organic group, $R^2$ is a divalent organic group, each $R^4$ is independently a hydrogen atom or a monovalent organic group, or two $R^4$ groups join to form a divalent organic group, and each $\alpha$ is independently an oxygen atom or a sulfur atom. In one or more embodiments, the divalent organic group $R^2$ may contain one or more additional silylated amino groups and/or one or more additional carboxylic or thiocarboxylic ester groups.

In one or more embodiments, where $R^3$ and an $R^4$ of formula I join to form a hydrocarbylene group, the carboxylic or thiocarboxylic esters containing a monosilylated amino group may be represented by the formula III:

where $R^1$ is a monovalent organic group, $R^2$ is a divalent organic group, $R^5$ is a hydrocarbylene group, each $R^4$ is independently a hydrogen atom or a monovalent organic group, and each $\alpha$ is independently an oxygen atom or a sulfur atom.

In one or more embodiments, where two $R^4$ groups of formula II join to form a divalent organic group, the carboxylic or thiocarboxylic esters containing a disilylated amino group may be represented by the formula IV:

where $R^1$ is a monovalent organic group, $R^2$ and $R^6$ are each independently a divalent organic group, each $R^4$ is independently a hydrogen atom or a monovalent organic group, and each $\alpha$ is independently an oxygen atom or a sulfur atom.

In one or more embodiments, the monovalent organic groups of the esters may be hydrocarbyl groups or substituted hydrocarbyl groups such as, but not limited to, alkyl, cycloalkyl, alkenyl, cycloalkenyl, aryl, allyl, aralkyl, alkaryl, or alkynyl groups. Substituted hydrocarbyl groups include hydrocarbyl groups in which one or more hydrogen atoms have been replaced by a substituent such as a hydrocarbyl, hydrocarbyloxy, silyl, or siloxy group. In one or more embodiments, these groups may include from one, or the appropriate minimum number of carbon atoms to form the group, to about 20 carbon atoms. These groups may also contain heteroatoms such as, but not limited to, nitrogen, boron, oxygen, silicon, sulfur, tin, and phosphorus atoms.

In one or more embodiments, the monovalent organic groups of the esters may be silyl groups or substituted silyl groups such as, but not limited to, trihydrocarbylsilyl, trisilyloxysilyl, trihydrocarbyloxysilyl, trisilylsilyl, dihydrocarbylhydrosilyl, dihydrocarbyl(silyloxy)silyl, dihydrocarbyl(silyl)silyl, dihydrocarbyl(hydrocarbyloxy)silyl, hydrocarbyldihydrosilyl, hydrocarbyl(disilyloxy)silyl, hydrocarbyl(disilyl)silyl, and hydrocarbyl(dihydrocarbyloxy)silyl groups. For example, types of silyl groups may include trialkylsilyl, dialkylhydrosilyl, dialkyl(silyloxy)silyl, dialkyl(silyl)silyl, tricycloalkylsilyl, dicycloalkylhydrosilyl, dicycloalkyl(silyloxy)silyl, dicycloalkyl(silyl)silyl, trialkenylsilyl, dialkenylhydrosilyl, dialkenyl(silyloxy)silyl, dialkenyl(silyl)silyl, tricycloalkenylsilyl, dicycloalkenylhydrosilyl, dicycloalkenyl(silyloxy)silyl, dicycloalkenyl(silyl)silyl, triarylsilyl, diarylhydrosilyl, diaryl(silyloxy)silyl, diaryl(silyl)silyl, triallylsilyl, diallylhydrosilyl, diallyl(silyloxy)silyl, diallyl(silyl)silyl, triaralkylsilyl, diaralkylhydrosilyl, diaralkyl(silyloxy)silyl, diaralkyl(silyl)silyl, trialkarylsilyl, dialkarylhydrosilyl, dialkaryl(silyloxy)silyl, dialkaryl(silyl)silyl, trialkynylsilyl, dialkynylhydrosilyl, dialkynyl(silyloxy)silyl, dialkynyl(silyl)silyl, tris(trialkylsilyloxy)silyl, tris(triarylsilyloxy)silyl, tris(tricycloalkylsilyloxy)silyl, tris(trialkoxysilyloxy)silyl, tris(triaryloxysilyloxy)silyl, or tris(tricycloalkyloxysilyloxy)silyl groups. Substituted silyl groups include silyl groups in which one or more hydrogen atoms have been replaced by a substituent such as a hydrocarbyl, hydrocarbyloxy, silyl, or siloxy group. In one or more embodiments, these groups may include from one, or the appropriate minimum number of carbon atoms to form the group, to about 20 carbon atoms. These groups may also contain heteroatoms such as, but not limited to, nitrogen, boron, oxygen, silicon, sulfur, tin, and phosphorus atoms.

In one or more embodiments, the divalent organic groups of the esters may include hydrocarbylene groups or substituted hydrocarbylene groups such as, but not limited to, alkylene, cycloalkylene, alkenylene, cycloalkenylene, alkynylene, cycloalkynylene, or arylene groups. Substituted hydrocarbylene groups include hydrocarbylene groups in which one or more hydrogen atoms have been replaced by a substituent such as an alkyl group. In one or more embodiments, these groups may include from one, or the appropriate minimum number of carbon atoms to form the group, to about 20 carbon atoms. These groups may also contain one or more heteroatoms such as, but not limited to, nitrogen, oxygen, boron, silicon, sulfur, tin, and phosphorus atoms.

In one or more embodiments, the divalent organic group $R^2$ is an acyclic divalent organic group (either linear or branched) that may or may not include one or more heteroatoms. In other embodiments, the divalent organic group $R^2$ is a heterocyclic divalent organic group. In yet other embodiments, the divalent organic group $R^2$ is a non-aromatic cyclic divalent organic group that is devoid of heteroatoms.

In one or more embodiments, the divalent organic group $R^2$ may contain an aromatic ring (e.g. a phenyl ring) that is devoid of heteroatoms so long as the silylated amino group is not directly attached to the aromatic ring (e.g. the silylated amino group can be attached to $R^2$ via an alkylene group pendent from the aromatic ring).

Exemplary types of carboxylic esters that contain a silylated amino group include those that derive from carboxylic esters such as arenecarboxylic esters, alkanecarboxylic esters, alkenecarboxylic esters, alkynecarboxylic esters, cycloalkanecarboxylic esters, cycloalkenecarboxylic esters, cycloalkynecarboxylic esters, and heterocyclic carboxylic esters. Exemplary types of thiocarboxylic esters that contain a silylated amino group include those that derive from thiocarboxylic esters such as arenethiocarboxylic esters, alkanethiocarboxylic esters, alkenethiocarboxylic esters, alkynethiocarboxylic esters, cycloalkanethiocarboxylic esters, cycloalkenethiocarboxylic esters, cycloalkynethiocarboxylic esters, and heterocyclic thiocarboxylic esters.

Exemplary arenecarboxylic esters containing a silylated amino group include those that derive from carboxylic esters such as hydrocarbyl 2-methylbenzoate, silyl 2-methylbenzoate, hydrocarbyl 3-methylbenzoate, silyl 3-methylbenzoate, hydrocarbyl 4-methylbenzoate, silyl 4-methylbenzoate, hydrocarbyl 2-ethylbenzoate, silyl 2-ethylbenzoate, hydrocarbyl 3-ethylbenzoate, silyl 3-ethylbenzoate, hydrocarbyl 4-ethylbenzoate, silyl 4-ethylbenzoate, hydrocarbyl 2-cyclohexylbenzoate, silyl 2-cyclohexylbenzoate, hydrocarbyl 3-cyclohexylbenzoate, silyl 3-cyclohexylbenzoate, hydrocarbyl 4-cyclohexylbenzoate, and silyl 4-cyclohexylbenzoate.

Exemplary alkanecarboxylic esters containing a silylated amino group include those that derive from carboxylic esters such as hydrocarbyl acetate, silyl acetate, hydrocarbyl propionate, silyl propionate, hydrocarbyl butyrate, silyl butyrate, hydrocarbyl isobutyrate, silyl isobutyrate, hydrocarbyl valerate, silyl valerate, hydrocarbyl isovalerate, silyl isovalerate, hydrocarbyl pivalate, silyl pivalate, hydrocarbyl hexanoate, silyl hexanoate, hydrocarbyl heptanoate, silyl heptanoate, dihydrocarbyl malonate, disilyl malonate, dihydrocarbyl succinate, disilyl succinate, dihydrocarbyl glutarate, and disilyl glutarate.

Exemplary alkenecarboxylic esters containing a silylated amino group include those that derive from carboxylic esters such as hydrocarbyl acrylate, silyl acrylate, hydrocarbyl methacrylate, silyl methacrylate, hydrocarbyl crotonate, silyl crotonate, hydrocarbyl 3-butenoate, silyl 3-butenoate, hydrocarbyl 2-methyl-2-butenoate, silyl 2-methyl-2-butenoate, hydrocarbyl 2-pentenoate, silyl 2-pentenoate, hydrocarbyl 3-pentenoate, silyl 3-pentenoate, hydrocarbyl 4-pentenoate, silyl 4-pentenoate, hydrocarbyl 5-hexenoate, silyl 5-hexenoate, hydrocarbyl 6-heptenoate, silyl 6-heptenoate, dihydrocarbyl fumarate, disilyl fumarate, dihydrocarbyl maleate, disilyl maleate, dihydrocarbyl methylenemalonate, disilyl methylenemalonate, dihydrocarbyl benzylidenemalonate, disilyl benzylidenemalonate dihydrocarbyl 2-methyleneglutarate, and disilyl 2-methyleneglutarate.

Exemplary alkynecarboxylic esters containing a silylated amino group include those that derive from carboxylic esters such as hydrocarbyl 3-butynoate, silyl 3-butynoate, hydrocarbyl 2-pentynoate, silyl 2-pentynoate, hydrocarbyl 3-pentynoate, silyl 3-pentynoate, hydrocarbyl 4-pentynoate, silyl 4-pentynoate, hydrocarbyl 5-hexynoate, and silyl 5-hexynoate.

Exemplary cycloalkanecarboxylic esters containing a silylated amino group include those that derive from carboxylic esters such as hydrocarbyl cyclopropanecarboxylate, silyl cyclopropanecarboxylate, hydrocarbyl cyclobutanecarboxylate, silyl cyclobutanecarboxylate, hydrocarbyl cyclopentanecarboxylate, silyl cyclopentanecarboxylate, hydrocarbyl cyclohexanecarboxylate, silyl cyclohexanecarboxylate, hydrocarbyl cycloheptanecarboxylate, and silyl cycloheptanecarboxylate.

Exemplary cycloalkenecarboxylic esters containing a silylated amino group include those that derive from carboxylic esters such as hydrocarbyl 1-cyclopropenecarboxylate, silyl 1-cyclopropenecarboxylate, hydrocarbyl 1-cyclobutenecarboxylate, silyl 1-cyclobutenecarboxylate, hydrocarbyl 1-cyclopentenecarboxylate, silyl 1-cyclopentenecarboxylate, hydrocarbyl 1-cyclohexenecarboxylate, silyl 1-cyclohexenecarboxylate, hydrocarbyl 1-cycloheptenecarboxylate, and silyl 1-cycloheptenecarboxylate.

Exemplary heterocyclic carboxylic esters containing a silylated amino group include those that derive from carboxylic esters such as hydrocarbyl 2-pyridinecarboxylate, silyl 2-pyridinecarboxylate, hydrocarbyl 3-pyridinecarboxylate, silyl 3-pyridinecarboxylate, hydrocarbyl 4-pyridinecarboxylate, silyl 4-pyridinecarboxylate, hydrocarbyl 2-pyrimidinecarboxylate, silyl 2-pyrimidinecarboxylate, hydrocarbyl 4-pyrimidinecarboxylate, silyl 4-pyrimidinecarboxylate, hydrocarbyl 5-pyrimidinecarboxylate, silyl 5-pyrimidinecarboxylate, hydrocarbyl pyrazinecarboxylate, silyl pyrazinecarboxylate, hydrocarbyl 3-pyridazinecarboxylate, silyl 3-pyridazinecarboxylate, hydrocarbyl 4-pyridazinecarboxylate, and silyl 4-pyridazinecarboxylate.

Exemplary arenethiocarboxylic esters containing a silylated amino group include those that derive from thiocarboxylic esters such as hydrocarbyl 2-methylthiobenzoate, silyl 2-methylthiobenzoate, hydrocarbyl 3-methylthiobenzoate, silyl 3-methylthiobenzoate, hydrocarbyl 4-methylthiobenzoate, silyl 4-methylthiobenzoate, hydrocarbyl 2-ethylthiobenzoate, silyl 2-ethylthiobenzoate, hydrocarbyl 3-ethylthiobenzoate, silyl 3-ethylthiobenzoate, hydrocarbyl 4-ethylthiobenzoate, silyl 4-ethylthiobenzoate, hydrocarbyl 2-cyclohexylthiobenzoate, silyl 2-cyclohexylthiobenzoate, hydrocarbyl 3-cyclohexylthiobenzoate, silyl 3-cyclohexylthiobenzoate, hydrocarbyl 4-cyclohexylthiobenzoate, and silyl 4-cyclohexylthiobenzoate.

Exemplary alkanethiocarboxylic esters containing a silylated amino group include those that derive from thiocarboxylic esters such as hydrocarbyl thioacetate, silyl thioacetate, hydrocarbyl thiopropionate, silyl thiopropionate, hydrocarbyl thiobutyrate, silyl thiobutyrate, hydrocarbyl thioisobutyrate, silyl thioisobutyrate, hydrocarbyl thiovalerate, silyl thiovalerate, hydrocarbyl thioisovalerate, silyl thioisovalerate, hydrocarbyl thiopivalate, silyl thiopivalate, hydrocarbyl thiohexanoate, silyl thiohexanoate, hydrocarbyl thioheptanoate, silyl thioheptanoate, dihydrocarbyl thiomalonate, disilyl thiomalonate, dihydrocarbyl thiosuccinate, disilyl thiosuccinate, dihydrocarbyl thioglutarate, and disilyl thioglutarate.

Exemplary alkenethiocarboxylic esters containing a silylated amino group include those that derive from thiocarboxylic esters such as hydrocarbyl thioacrylate, silyl thioacrylate, hydrocarbyl thiomethacrylate, silyl thiomethacrylate, hydrocarbyl thiocrotonate, silyl thiocrotonate, hydrocarbyl 3-thiobutenoate, silyl 3-thiobutenoate, hydrocarbyl 2-methyl-2-thiobutenoate, silyl 2-methyl-2-thiobutenoate, hydrocarbyl 2 thiopentenoate, silyl 2-thiopentenoate, hydrocarbyl 3-thiopentenoate, silyl 3-thiopentenoate, hydrocarbyl 4-thiopentenoate, silyl 4-thiopentenoate, hydrocarbyl 5-thiohexenoate, silyl 5-thiohexenoate, hydrocarbyl 6-thioheptenoate, silyl 6-thioheptenoate, dihydrocarbyl thiofumarate, disilyl thiofumarate, dihydrocarbyl thiomaleate, disilyl thiomaleate, dihydrocarbyl methylenethiomalonate, disilyl methylenethiomalonate, dihydrocarbyl benzylidenethiomalonate, disilyl benzylidenethiomalonate dihydrocarbyl 2-methylenethioglutarate, and disilyl 2-methylenethioglutarate.

Exemplary alkynethiocarboxylic esters containing a silylated amino group include those that derive from thiocarboxylic esters such as hydrocarbyl 3-thiobutynoate, silyl 3-thiobutynoate, hydrocarbyl 2-thiopentynoate, silyl 2-thiopentynoate, hydrocarbyl 3-thiopentynoate, silyl 3-thiopentynoate, hydrocarbyl 4-thiopentynoate, silyl 4-thiopentynoate, hydrocarbyl 5-thiohexynoate, and silyl 5-thiohexynoate.

Exemplary cycloalkanethiocarboxylic esters containing a silylated amino group include those that derive from thiocarboxylic esters such as hydrocarbyl cyclopropanethiocarboxylate, silyl cyclopropanethiocarboxylate, hydrocarbyl cyclobutanethiocarboxylate, silyl cyclobutanethiocarboxylate, hydrocarbyl cyclopentanethiocarboxylate, silyl cyclopentanethiocarboxylate, hydrocarbyl cyclohexanethiocarboxylate, silyl cyclohexanethiocarboxylate, hydrocarbyl cycloheptanethiocarboxylate, and silyl cycloheptanethiocarboxylate.

Exemplary cycloalkenethiocarboxylic esters containing a silylated amino group include those that derive from thiocarboxylic esters such as hydrocarbyl 1-cyclopropenethiocarboxylate, silyl 1-cyclopropenethiocarboxylate, hydrocarbyl 1-cyclobutenethiocarboxylate, silyl 1-cyclobuntenethiocarboxylate, hydrocarbyl 1-cyclopentenethiocarboxylate, silyl 1-cyclopentenethiocarboxylate, hydrocarbyl 1-cyclohexenethiocarboxylate, silyl 1-cyclohexenethiocarboxylate, hydrocarbyl 1-cycloheptenethiocarboxylate, and silyl 1-cycloheptenethiocarboxylate.

Exemplary heterocyclic thiocarboxylic esters containing a silylated amino group include those that derive from thiocarboxylic esters such as hydrocarbyl 2-pyridinethiocarboxylate, silyl 2-pyridinethiocarboxylate, hydrocarbyl 3-pyridinethiocarboxylate, silyl 3-pyridinethiocarboxylate, hydrocarbyl 4 pyridinethiocarboxylate, silyl 4-pyridinethiocarboxylate, hydrocarbyl 2-pyrimidinethiocarboxylate, silyl 2-pyrimidinethiocarboxylate, hydrocarbyl 4-pyrimidinethiocarboxylate, silyl 4-pyrimidinethiocarboxylate, hydrocarbyl 5-pyrimidinethiocarboxylate, silyl 5-pyrimidinethiocarboxylate, hydrocarbyl pyrazinethiocarboxylate, silyl pyrazinethiocarboxylate, hydrocarbyl 3-pyridazinethiocarboxylate, silyl 3-pyridazinethiocarboxylate, hydrocarbyl 4-pyridazinethiocarboxylate, and silyl 4-pyridazinethiocarboxylate.

Exemplary types of arenecarboxylic esters containing a silylated amino group include [bis(trihydrocarbylsilyl)amino]arenecarboxylic esters, [bis(dihydrocarbylhydrosilyl)amino]arenecarboxylic esters, (1-aza-disila-1-cyclohydrocarbyl)arenecarboxylic esters, [(trihydrocarbylsilyl)(hydrocarbyl)amino]arenecarboxylic esters, [(dihydrocarbylhydrosilyl)(hydrocarbyl)amino]arenecarboxylic esters, (1-aza-2-sila-1-cyclohydrocarbyl)arenecarboxylic esters, (dihydrocarbylamino)arenecarboxylic esters, and (1-aza-1-cyclohydrocarbyl)arenecarboxylic esters.

Exemplary types of alkanecarboxylic esters containing a silylated amino group include [bis(trihydrocarbylsilyl)amino]alkanecarboxylic esters, [bis(dihydrocarbylhydrosilyl)amino]alkanecarboxylic esters, (1-aza-disila-1-cyclohydrocarbyl)alkanecarboxylic esters, [(trihydrocarbylsilyl)(hydrocarbyl)amino]alkanecarboxylic esters, [(dihydrocarbylhydrosilyl)(hydrocarbyl)amino]alkanecarboxylic esters, and (1-aza-2-sila-1-cyclohydrocarbyl)alkanecarboxylic esters.

Exemplary types of alkenecarboxylic esters containing a silylated amino group include [bis(trihydrocarbylsilyl)amino]alkenecarboxylic esters, [bis(dihydrocarbylhydrosilyl)amino]alkenecarboxylic esters, (1-aza-disila-1-cyclohydrocarbyl)alkenecarboxylic esters, [(trihydrocarbylsilyl)(hydrocarbyl)amino]alkenecarboxylic esters, [(dihydrocarbylhydrosilyl)(hydrocarbyl)amino]alkenecarboxylic esters, and (1-aza-2-sila-1-cyclohydrocarbyl)alkenecarboxylic esters.

Exemplary types of alkynecarboxylic esters containing a silylated amino group include [bis(trihydrocarbylsilyl)amino]alkynecarboxylic esters, [bis(dihydrocarbylhydrosilyl)amino]alkynecarboxylic esters, (1-aza-disila-1-cyclohydrocarbyl)alkynecarboxylic esters, [(trihydrocarbylsilyl)(hydrocarbyl)amino]alkynecarboxylic esters,

[(dihydrocarbylhydrosilyl)(hydrocarbyl)amino]alkynecarboxylic esters, and (1-aza-2-sila-1-cyclohydrocarbyl)alkynecarboxylic esters.

Exemplary types of cycloalkanecarboxylic esters containing a silylated amino group include [bis(trihydrocarbylsilyl)amino]cycloalkanecarboxylic esters, [bis(dihydrocarbylhydrosilyl)amino]cycloalkanecarboxylic esters, (1-aza-disila-1-cyclohydrocarbyl)cycloalkanecarboxylic esters, [(trihydrocarbylsilyl)(hydrocarbyl)amino]cycloalkanecarboxylic esters, [(dihydrocarbylhydrosilyl)(hydrocarbyl)amino]cycloalkanecarboxylic esters, and (1-aza-2-sila-1-cyclohydrocarbyl)cycloalkanecarboxylic esters.

Exemplary types of cycloalkenecarboxylic esters containing a silylated amino group include [bis(trihydrocarbylsilyl)amino]cycloalkenecarboxylic esters, [bis(dihydrocarbylhydrosilyl)amino]cycloalkenecarboxylic esters, (1-aza-disila-1-cyclohydrocarbyl)cycloalkenecarboxylic esters, [(trihydrocarbylsilyl)(hydrocarbyl)amino]cycloalkenecarboxylic esters, [(dihydrocarbylhydrosilyl)(hydrocarbyl)amino]cycloalkenecarboxylic esters, and (1-aza-2-sila-1-cyclohydrocarbyl)cycloalkenecarboxylic esters.

Exemplary types of cycloalkynecarboxylic esters containing a silylated amino group include [bis(trihydrocarbylsilyl)amino]cycloalkynecarboxylic esters, [bis(dihydrocarbylhydrosilyl)amino]cycloalkynecarboxylic esters, (1-aza-disila-1-cyclohydrocarbyl)cycloalkynecarboxylic esters, [(trihydrocarbylsilyl)(hydrocarbyl)amino]cycloalkynecarboxylic esters, [(dihydrocarbylhydrosilyl)(hydrocarbyl)amino]cycloalkynecarboxylic esters, and (1-aza-2-sila-1-cyclohydrocarbyl)cycloalkynecarboxylic esters.

Exemplary types of heterocyclic carboxylic esters containing a silylated amino group include [bis(trihydrocarbylsilyl)amino]heterocyclic carboxylic esters, [bis(dihydrocarbylhydrosilyl)amino]heterocyclic carboxylic esters, (1-aza-disila-1-cyclohydrocarbyl)heterocyclic carboxylic esters, [(trihydrocarbylsilyl)(hydrocarbyl)amino]heterocyclic carboxylic esters, [(dihydrocarbylhydrosilyl)(hydrocarbyl)amino]heterocyclic carboxylic esters, and (1-aza-2-sila-1-cyclohydrocarbyl)heterocyclic carboxylic esters.

Exemplary types of arenethiocarboxylic esters containing a silylated amino group include [bis(trihydrocarbylsilyl)amino]arenethiocarboxylic esters, [bis(dihydrocarbylhydrosilyl)amino]arenethiocarboxylic esters, (1-aza-disila-1-cyclohydrocarbyl)arenethiocarboxylic esters, [(trihydrocarbylsilyl)(hydrocarbyl)amino]arenethiocarboxylic esters, [(dihydrocarbylhydrosilyl)(hydrocarbyl)amino]arenethiocarboxylic esters, (1-aza-2-sila-1-cyclohydrocarbyl)arenethiocarboxylic esters, (dihydrocarbylamino)arenethiocarboxylic esters, and (1-aza-1-cyclohydrocarbyl)arenethiocarboxylic esters.

Exemplary types of alkanethiocarboxylic esters containing a silylated amino group include [bis(trihydrocarbylsilyl)amino]alkanethiocarboxylic esters, [bis(dihydrocarbylhydrosilyl)amino]alkanethiocarboxylic esters, (1-aza-disila-1-cyclohydrocarbyl)alkanethiocarboxylic esters, [(trihydrocarbylsilyl)(hydrocarbyl)amino]alkanethiocarboxylic esters, [(dihydrocarbylhydrosilyl)(hydrocarbyl)amino]alkanethiocarboxylic esters, and (1-aza-2-sila-1-cyclohydrocarbyl)alkanethiocarboxylic esters.

Exemplary types of alkenethiocarboxylic esters containing a silylated amino group include [bis(trihydrocarbylsilyl)amino]alkenethiocarboxylic esters, [bis(dihydrocarbylhydrosilyl)amino]alkenethiocarboxylic esters, (1-aza-disila-1-cyclohydrocarbyl)alkenethiocarboxylic esters, [(trihydrocarbylsilyl)(hydrocarbyl)amino]alkenethiocarboxylic esters, [(dihydrocarbylhydrosilyl)(hydrocarbyl)amino]alkenethiocarboxylic esters, and (1-aza-2-sila-1-cyclohydrocarbyl)alkenethiocarboxylic esters.

Exemplary types of alkynethiocarboxylic esters containing a silylated amino group include [bis(trihydrocarbylsilyl)amino]alkynethiocarboxylic esters, [bis(dihydrocarbylhydrosilyl)amino]alkynethiocarboxylic esters, (1-aza-disila-1-cyclohydrocarbyl)alkynethiocarboxylic esters, [(trihydrocarbylsilyl)(hydrocarbyl)amino]alkynethiocarboxylic esters, [(dihydrocarbylhydrosilyl)(hydrocarbyl)amino]alkynethiocarboxylic esters, and (1-aza-2-sila-1-cyclohydrocarbyl)alkynethiocarboxylic esters.

Exemplary types of cycloalkanethiocarboxylic esters containing a silylated amino group include [bis(trihydrocarbylsilyl)amino]cycloalkanethiocarboxylic esters, [bis(dihydrocarbylhydrosilyl)amino]cycloalkanethiocarboxylic esters, (1-aza-disila-1-cyclohydrocarbyl)cycloalkanethiocarboxylic esters, [(trihydrocarbylsilyl)(hydrocarbyl)amino]cycloalkanethiocarboxylic esters, [(dihydrocarbylhydrosilyl)(hydrocarbyl)amino]cycloalkanethiocarboxylic esters, and (1-aza-2-sila-1-cyclohydrocarbyl)cycloalkanethiocarboxylic esters.

Exemplary types of cycloalkenethiocarboxylic esters containing a silylated amino group include [bis(trihydrocarbylsilyl)amino]cycloalkenethiocarboxylic esters, [bis(dihydrocarbylhydrosilyl)amino]cycloalkenethiocarboxylic esters, (1-aza-disila-1-cyclohydrocarbyl)cycloalkenethiocarboxylic esters, [(trihydrocarbylsilyl)(hydrocarbyl)amino]cycloalkenethiocarboxylic esters, [(dihydrocarbylhydrosilyl)(hydrocarbyl)amino]cycloalkenethiocarboxylic esters, and (1-aza-2-sila-1-cyclohydrocarbyl)cycloalkenethiocarboxylic esters.

Exemplary types of cycloalkynethiocarboxylic esters containing a silylated amino group include [bis(trihydrocarbylsilyl)amino]cycloalkynethiocarboxylic esters, [bis(dihydrocarbylhydrosilyl)amino]cycloalkynethiocarboxylic esters, (1-aza-disila-1-cyclohydrocarbyl)cycloalkynethiocarboxylic esters, [(trihydrocarbylsilyl)(hydrocarbyl)amino]cycloalkynethiocarboxylic esters, [(dihydrocarbylhydrosilyl)(hydrocarbyl)amino]cycloalkynethiocarboxylic esters, and (1-aza-2-sila-1-cyclohydrocarbyl)cycloalkynethiocarboxylic esters.

Exemplary types of heterocyclic thiocarboxylic esters containing a silylated amino group include [bis(trihydrocarbylsilyl)amino]heterocyclic thiocarboxylic esters, [bis(dihydrocarbylhydrosilyl)amino]heterocyclic thiocarboxylic esters, (1-aza-disila-1-cyclohydrocarbyl)heterocyclic thiocarboxylic esters, [(trihydrocarbylsilyl)(hydrocarbyl)amino]heterocyclic thiocarboxylic esters, [(dihydrocarbylhydrosilyl)(hydrocarbyl)amino]heterocyclic thiocarboxylic esters, and (1-aza-2-sila-1-cyclohydrocarbyl)heterocyclic thiocarboxylic esters.

Specific examples of arenecarboxylic esters containing a silylated amino group include ethyl 2-[bis(trimethylsilyl)aminomethyl]benzoate, ethyl 3-[bis(trimethylsilyl)aminomethyl]benzoate, ethyl 4-[bis(trimethylsilyl)aminomethyl]benzoate, phenyl 3-[bis(trimethylsilyl)aminomethyl]benzoate, trimethylsilyl 4-[bis(trimethylsilyl)aminomethyl]benzoate, ethyl 2-[(2,2,5,5-tetramethyl-1-aza-2,5-disila-1-cyclopentyl)methyl]benzoate, phenyl 3-[(2,2,5,5-tetramethyl-1-aza-2,5-disila-1-cyclopentyl)methyl]benzoate, trimethylsilyl 4-[(2,2,5,5-tetramethyl-1-aza-2,5-disila-1-cyclopentyl)methyl]benzoate, ethyl 2-[(trimethylsilyl)(methyl)aminomethyl]benzoate, phenyl 3-[(trimethylsilyl)(methyl)aminomethyl]benzoate, trimethylsilyl 4-[(trimethylsilyl)(methyl)aminomethyl]benzoate, ethyl 2-[(2,2-dimethyl-1-aza-2-sila-1-cyclopentyl)methyl]benzoate, phenyl 3-[(2,2-dimethyl-1-aza-2-sila-1-cyclopentyl)methyl]benzoate, and trimethylsilyl 4-[(2,2-dimethyl-1-aza-2-sila-1-cyclopentyl)methyl]benzoate.

Specific examples of alkanecarboxylic esters containing a silylated amino group include ethyl[bis(trimethylsilyl)amino]acetate, ethyl 3-[bis(trimethylsilyl)amino]propionate, triethyl[3-[bis(trimethylsilyl)amino]propyl]methanetricarboxylate, phenyl 3-[bis(trimethylsilyl)amino]propionate, trimethylsilyl 4-[bis(trimethylsilyl)amino]butyrate, ethyl 5-[bis(trimethylsilyl)amino]valerate, phenyl(2,2,5,5-tetramethyl-1-aza-2,5-disila-1-cyclopentyl)acetate, triethyl[3-(2,2,5,5-tetramethyl-1-aza-2,5-disila-1-cyclopentyl)propyl]methanetricarboxylate, trimethylsilyl 3-(2,2,5,5-tetramethyl-1-aza-2,5-disila-1-cyclopentyl)propionate, ethyl 4-(2,2,5,5-tetramethyl-1-aza-2,5-disila-1-cyclopentyl)butyrate, phenyl 5-(2,2,5,5-tetramethyl-1-aza-2,5-disila-1-cyclopentyl)valerate, trimethylsilyl[(trimethylsilyl)(methyl)amino]acetate, ethyl[(trimethylsilyl)(ethyl)amino]acetate, phenyl 3-[(trimethylsilyl)(methyl)amino]propionate, trimethylsilyl 3-[(trimethylsilyl)(ethyl)amino]propionate, ethyl 4-[(trimethylsilyl)(methyl)amino]butyrate, phenyl 4-[(trimethylsilyl)(ethyl)amino]butyrate, trimethylsilyl 5-[(trimethylsilyl)(methyl)amino]valerate, ethyl 5-[(trimethylsilyl)(ethyl)amino]valerate, ethyl(2,2-dimethyl-1-aza-2-sila-1-cyclopentyl)acetate, phenyl 3-(2,2-dimethyl-1-aza-2-sila-1-cyclopentyl)propionate, trimethylsilyl 4-(2,2-dimethyl-1-aza-2-sila-1-cyclopentyl)butyrate, and ethyl 5-(2,2-dimethyl-1-aza-2-sila-1-cyclopentyl)valerate.

Specific examples of alkenecarboxylic esters containing a silylated amino group include ethyl 3-[bis(trimethylsilyl)amino]crotonate, phenyl 3-[bis(trimethylsilyl)amino]-4-pentenoate, trimethylsilyl 3-[bis(trimethylsilyl)amino]-5-hexenoate, ethyl 3-(2,2,5,5-tetramethyl-1-aza-2,5-disila-1-cyclopentyl)crotonate, phenyl 3-(2,2,5,5-tetramethyl-1-aza-2,5-disila-1-cyclopentyl)-4-pentenoate, trimethylsilyl 3-(2,2,5,5-tetramethyl-1-aza-2,5-disila-1-cyclopentyl)-5-hexenoate, ethyl 3-[(trimethylsilyl)(methyl)amino]crotonate, phenyl 3-[(trimethylsilyl)(ethyl)amino]crotonate, trimethylsilyl 3-[(trimethylsilyl)(methyl)amino]-4-pentenoate, ethyl 3-[(trimethylsilyl)(ethyl)amino]-4-pentenoate, phenyl 3-[(trimethylsilyl)(methyl)amino]-5-hexenoate, trimethylsilyl 3-[(trimethylsilyl)(ethyl)amino]-5-hexenoate, ethyl 3-(2,2-dimethyl-1-aza-2-sila-1-cyclopentyl)crotonate, phenyl 3-(2,2-dimethyl-1-aza-2-sila-1-cyclopentyl)-4-pentenoate, and trimethylsilyl 3-(2,2-dimethyl-1-aza-2-sila-1-cyclopentyl)-5-hexenoate.

Specific examples of alkynecarboxylic esters containing a silylated amino group include ethyl 3-[bis(trimethylsilyl)amino]-4-pentynoate, phenyl 3-[bis(trimethylsilyl)amino]-5-hexynoate, trimethylsilyl 3-(2,2,5,5-tetramethyl-1-aza-2,5-disila-1-cyclopentyl)-4-pentynoate, ethyl 3-(2,2,5,5-tetramethyl-1-aza-2,5-disila-1-cyclopentyl)-5-hexynoate, phenyl 3-[(trimethylsilyl)(methyl)amino]-4-pentynoate, trimethylsilyl 3-[(trimethylsilyl)(ethyl)amino]-4-pentynoate, ethyl 3-[(trimethylsilyl)(methyl)amino]-5-hexynoate, phenyl 3-[(trimethylsilyl)(ethyl)amino]-5-hexynoate, trimethylsilyl 3-(2,2-dimethyl-1-aza-2-sila-1-cyclopentyl)-4-pentynoate, and ethyl 3-(2,2-dimethyl-1-aza-2-sila-1-cyclopentyl)-5-hexynoate.

Specific examples of cycloalkanecarboxylic esters containing a silylated amino group include ethyl 2-[bis(trimethylsilyl)amino]cyclopentanecarboxylate, ethyl 3-[bis(trimethylsilyl)amino]cyclopentanecarboxylate, ethyl 2-[bis(trimethylsilyl)amino]cyclohexanecarboxylate, ethyl 3-[bis(trimethylsilyl)amino]cyclohexanecarboxylate, ethyl 4-[bis(trimethylsilyl)amino]cyclohexanecarboxylate, phenyl 4-[bis(trimethylsilyl)amino]cyclohexanecarboxylate, trimethylsilyl 3-(2,2,5,5-tetramethyl-1-aza-2,5-disila-1-cyclopentyl)cyclopentanecarboxylate, ethyl 4-(2,2,5,5-tetramethyl-1-aza-2,5-disila-1-cyclopentyl)cyclohexanecarboxylate, phenyl 3-[(trimethylsilyl)(methyl)amino]cyclopentanecarboxylate, trimethylsilyl 3-[(trimethylsilyl)(ethyl)amino]cyclopentanecarboxylate, ethyl 4-[(trimethylsilyl)(methyl)amino]cyclohexanecarboxylate, phenyl 4-[(trimethylsilyl)(ethyl)amino]cyclohexanecarboxylate, trimethylsilyl 3-(2,2-dimethyl-1-aza-2-sila-1-cyclopentyl)cyclopentanecarboxylate, and ethyl 4-(2,2-dimethyl-1-aza-2-sila-1-cyclopentyl)cyclohexanecarboxylate.

Specific examples of cycloalkenecarboxylic esters containing a silylated amino group include ethyl 4-[bis(trimethylsilyl)amino]cyclopentene-1-carboxylate, phenyl 4-[bis(trimethylsilyl)amino]cyclohexene-1-carboxylate, trimethylsilyl 4-(2,2,5,5-tetramethyl-1-aza-2,5-disila-1-cyclopentyl)cyclopentene-1-carboxylate, ethyl 4-(2,2,5,5-tetramethyl-1-aza-2,5-disila-1-cyclopentyl)cyclohexene-1-carboxylate, phenyl 4-[(trimethylsilyl)(methyl)amino]cyclopentene-1-carboxylate, trimethylsilyl 4-[(trimethylsilyl)(ethyl)amino]cyclopentene-1-carboxylate, ethyl 4-[(trimethylsilyl)(methyl)amino]cyclohexene-1-carboxylate, phenyl 4-[(trimethylsilyl)(ethyl)amino]cyclohexene-1-carboxylate, trimethylsilyl 4-(2,2-dimethyl-1-aza-2-sila-1-cyclopentyl)cyclopentene-1-carboxylate, and ethyl 4-(2,2-dimethyl-1-aza-2-sila-1-cyclopentyl)cyclohexene-1-carboxylate.

Specific examples of heterocyclic carboxylic esters containing a silylated amino group include ethyl 5-[bis(trimethylsilyl)amino]-2-pyridinecarboxylate, phenyl 5-[bis(trimethylsilyl)amino]-2-pyrimidinecarboxylate, trimethylsilyl 5-(2,2,5,5-tetramethyl-1-aza-2,5-disila-1-cyclopentyl)-2-pyridinecarboxylate, ethyl 5-(2,2,5,5-tetramethyl-1-aza-2,5-disila-1-cyclopentyl)-2-pyrimidinecarboxylate, phenyl 5-[(trimethylsilyl)(methyl)amino]-2-pyridinecarboxylate, trimethylsilyl 5-[(trimethylsilyl)(ethyl)amino]-2-pyridinecarboxylate, ethyl 5-[(trimethylsilyl)(methyl)amino]-2-pyrimidinecarboxylate, phenyl 5-[(trimethylsilyl)(ethyl)amino]-2-pyrimidinecarboxylate, trimethylsilyl 5-(2,2-dimethyl-1-aza-2-sila-1-cyclopentyl)-2-pyridinecarboxylate, and ethyl 5-(2,2-dimethyl-1-aza-2-sila-1-cyclopentyl)-2-pyrimidinecarboxylate.

Specific examples of arenethiocarboxylic esters containing a silylated amino group include ethyl 2-[bis(trimethylsilyl)aminomethyl]thiobenzoate, ethyl 3-[bis(trimethylsilyl)aminomethyl]thiobenzoate, ethyl 4-[bis(trimethylsilyl)aminomethyl]thiobenzoate, phenyl 3-[bis(trimethylsilyl)aminomethyl]thiobenzoate, trimethylsilyl 4-[bis(trimethylsilyl)aminomethyl]thiobenzoate, ethyl 2-[(2,2,5,5-tetramethyl-1-aza-2,5-disila-1-cyclopentyl)methyl]thiobenzoate, phenyl 3-[(2,2,5,5-tetramethyl-1-aza-2,5-disila-1-cyclopentyl)methyl]thiobenzoate, trimethylsilyl 4-[(2,2,5,5-tetramethyl-1-aza-2,5-disila-1-cyclopentyl)methyl]thiobenzoate, ethyl 2-[(trimethylsilyl)(methyl)aminomethyl]thiobenzoate, phenyl 3-[(trimethylsilyl)(methyl)aminomethyl]thiobenzoate, trimethylsilyl 4-[(trimethylsilyl)(methyl)aminomethyl]thiobenzoate, ethyl 2-[(2,2-dimethyl-1-aza-2-sila-1-cyclopentyl)methyl]thiobenzoate, phenyl 3-[(2,2-dimethyl-1-aza-2-sila-1-cyclopentyl)methyl]thiobenzoate, and trimethylsilyl 4-[(2,2-dimethyl-1-aza-2-sila-1-cyclopentyl)methyl]thiobenzoate.

Specific examples of alkanethiocarboxylic esters containing a silylated amino group include ethyl[bis(trimethylsilyl)amino]thioacetate, ethyl 3-[bis(trimethylsilyl)amino]thiopropionate, phenyl 3-[bis(trimethylsilyl)amino]thiopropionate, trimethylsilyl 4-[bis(trimethylsilyl)amino]thiobutyrate, ethyl 5-[bis(trimethylsilyl)amino]thiovalerate, phenyl(2,2,5,5-tetramethyl-1-aza-2,5-disila-1-cyclopentyl) thioacetate, trimethylsilyl 3-(2,2,5,5-tetramethyl-1-aza-2,5-disila-1-cyclopentyl)thiopropionate, ethyl 4-(2,2,5,5-tetramethyl-1-aza-2,5-disila-1-cyclopentyl)thiobutyrate, phenyl 5-(2,2,5,5-tetramethyl-1-aza-2,5-disila-1-cyclopentyl)thiovalerate, trimethylsilyl[(trimethylsilyl)(methyl)amino]thioacetate, ethyl [(trimethylsilyl)(ethyl)amino]thioacetate, phenyl 3-[(trimethylsilyl)(methyl)amino]thiopropionate, trimethylsilyl 3-[(trimethylsilyl)(ethyl)amino]thiopropionate, ethyl 4-[(trimethylsilyl)(methyl)amino]thiobutyrate, phenyl 4-[(trimethylsilyl)(ethyl)amino]thiobutyrate, trimethylsilyl 5-[(trimethylsilyl)(methyl)amino]thiovalerate, ethyl 5-[(trimethylsilyl)(ethyl)amino]thiovalerate, ethyl(2,2-dimethyl-1-aza-2-sila-1-cyclopentyl)thioacetate, phenyl 3-(2,2-dimethyl-1-aza-2-sila-1-cyclopentyl)thiopropionate, trimethylsilyl 4-(2,2-dimethyl-1-aza-2-sila-1-cyclopentyl) thiobutyrate, and ethyl 5-(2,2-dimethyl-1-aza-2-sila-1-cyclopentyl)thiovalerate.

Specific examples of alkenethiocarboxylic esters containing a silylated amino group include ethyl 3-[bis(trimethylsilyl)amino]thiocrotonate, phenyl 3-[bis(trimethylsilyl)amino]-4-thiopentenoate, trimethylsilyl 3-[bis(trimethylsilyl)amino]-5-thiohexenoate, ethyl 3-(2,2,5,5-tetramethyl-1-aza-2,5-disila-1-cyclopentyl)thiocrotonate, phenyl 3-(2,2,5,5-tetramethyl-1-aza-2,5-disila-1-cyclopentyl)-4-thiopentenoate, trimethylsilyl 3-(2,2,5,5-tetramethyl-1-aza-2,5-disila-1-cyclopentyl)-5-thiohexenoate, ethyl 3-[(trimethylsilyl)(methyl)amino]thiocrotonate, phenyl 3-[(trimethylsilyl)(ethyl)amino]thiocrotonate, trimethylsilyl 3-[(trimethylsilyl)(methyl)amino]-4-thiopentenoate, ethyl 3-[(trimethylsilyl)(ethyl)amino]-4-thiopentenoate, phenyl 3-[(trimethylsilyl)(methyl)amino]-5-thiohexenoate, trimethylsilyl 3-[(trimethylsilyl)(ethyl)amino]-5-thiohexenoate, ethyl 3-(2,2-dimethyl-1-aza-2-sila-1-cyclopentyl)thiocrotonate, phenyl 3-(2,2-dimethyl-1-aza-2-sila-1-cyclopentyl)-4-thiopentenoate, and trimethylsilyl 3-(2,2-dimethyl-1-aza-2-sila-1-cyclopentyl)-5-thiohexenoate.

Specific examples of alkynethiocarboxylic esters containing a silylated amino group include ethyl 3-[bis(trimethylsilyl)amino]-4-thiopentynoate, phenyl 3-[bis(trimethylsilyl)amino]-5-thiohexynoate, trimethylsilyl 3-(2,2,5,5-tetramethyl-1-aza-2,5-disila-1-cyclopentyl)-4-thiopentynoate, ethyl 3-(2,2,5,5-tetramethyl-1-aza-2,5-disila-1-cyclopentyl)-5-thiohexynoate, phenyl 3-[(trimethylsilyl)(methyl)amino]-4-thiopentynoate, trimethylsilyl 3-[(trimethylsilyl)(ethyl)amino]-4-thiopentynoate, ethyl 3-[(trimethylsilyl)(methyl)amino]-5-thiohexynoate, phenyl 3-[(trimethylsilyl)(ethyl)amino]-5-thiohexynoate, trimethylsilyl 3-(2,2-dimethyl-1-aza-2-sila-1-cyclopentyl)-4-thiopentynoate, and ethyl 3-(2,2-dimethyl-1-aza-2-sila-1-cyclopentyl)-5-thiohexynoate.

Specific examples of cycloalkanethiocarboxylic esters containing a silylated amino group include ethyl 2-[bis(trimethylsilyl)amino]cyclopentanethiocarboxylate, ethyl 3-[bis(trimethylsilyl)amino]cyclopentanethiocarboxylate, ethyl 2-[bis(trimethylsilyl)amino]cyclohexanethiocarboxylate, ethyl 3-[bis(trimethylsilyl)amino]cyclohexanethiocarboxylate, ethyl 4-[bis(trimethylsilyl)amino]cyclohexanethiocarboxylate, phenyl 4-[bis(trimethylsilyl)amino]cyclohexanethiocarboxylate, trimethylsilyl 3-(2,2,5,5-tetramethyl-1-aza-2,5-disila-1-cyclopentyl)cyclopentanethiocarboxylate, ethyl 4-(2,2,5,5-tetramethyl-1-aza-2,5-disila-1-cyclopentyl)cyclohexanethiocarboxylate, phenyl 3-[(trimethylsilyl)(methyl)amino]cyclopentanethiocarboxylate, trimethylsilyl 3-[(trimethylsilyl)(ethyl)amino]cyclopentanethiocarboxylate, ethyl 4-[(trimethylsilyl)(methyl)amino]cyclohexanethiocarboxylate, phenyl 4-[(trimethylsilyl)(ethyl)amino]cyclohexanethiocarboxylate, trimethylsilyl 3-(2,2-dimethyl-1-aza-2-sila-1-cyclopentyl)cyclopentanethiocarboxylate, and ethyl 4-(2,2-dimethyl-1-aza-2-sila-1-cyclopentyl)cyclohexanethiocarboxylate.

Specific examples of cycloalkenethiocarboxylic esters containing a silylated amino group include ethyl 4-[bis(trimethylsilyl)amino]cyclopentene-1-thiocarboxylate, phenyl 4-[bis(trimethylsilyl)amino]cyclohexene-1-thiocarboxylate, trimethylsilyl 4-(2,2,5,5-tetramethyl-1-aza-2,5-disila-1-cyclopentyl)cyclopentene-1-thiocarboxylate, ethyl 4-(2,2,5,5-tetramethyl-1-aza-2,5-disila-1-cyclopentyl)cyclohexene-1-thiocarboxylate, phenyl 4-[(trimethylsilyl)(methyl)amino]cyclopentene-1-thiocarboxylate, trimethylsilyl 4-[(trimethylsilyl)(ethyl)amino]cyclopentene-1-thiocarboxylate, ethyl 4-[(trimethylsilyl)(methyl)amino]cyclohexene-1-thiocarboxylate, phenyl 4-[(trimethylsilyl)(ethyl)amino]cyclohexene-1-thiocarboxylate, trimethylsilyl 4-(2,2-dimethyl-1-aza-2-sila-1-cyclopentyl)cyclopentene-1-thiocarboxylate, and ethyl 4-(2,2-dimethyl-1-aza-2-sila-1-cyclopentyl)cyclohexene-1-thiocarboxylate.

Specific examples of heterocyclic thiocarboxylic esters containing a silylated amino group include ethyl 5-[bis(trimethylsilyl)amino]-2-pyridinethiocarboxylate, phenyl 5-[bis(trimethylsilyl)amino]-2-pyrimidinethiocarboxylate, trimethylsilyl 5-(2,2,5,5-tetramethyl-1-aza-2,5-disila-1-cyclopentyl)-2-pyridinethiocarboxylate, ethyl 5-(2,2,5,5-tetramethyl-1-aza-2,5-disila-1-cyclopentyl)-2-pyrimidinethiocarboxylate, phenyl 5-[(trimethylsilyl)(methyl)amino]-2-pyridinethiocarboxylate, trimethylsilyl 5-[(trimethylsilyl)(ethyl)amino]-2-pyridinethiocarboxylate, ethyl 5-[(trimethylsilyl)(methyl)amino]-2-pyrimidinethiocarboxylate, phenyl 5-[(trimethylsilyl)(ethyl)amino]-2-pyrimidinethiocarboxylate, trimethylsilyl 5-(2,2-dimethyl-1-aza-2-sila-1-cyclopentyl)-2-pyridinethiocarboxylate, and ethyl 5-(2,2-dimethyl-1-aza-2-sila-1-cyclopentyl)-2-pyrimidinethiocarboxylate.

In one or more embodiments, the carboxylic or thiocarboxylic esters containing a silylated amino group can be synthesized by silylating a carboxylic or thiocarboxylic ester containing a primary amino group (i.e. —NH$_2$) or a secondary amino group represented by the formula —NH(R), where R is a monovalent organic group such as a hydrocarbyl or silyl group. Exemplary silylating reagents include trialkylsilyl halides, 1,2-bis(chlorodimethylsilyl)ethane, and trialkylsilyl trifluoromethanesulfonate. A base, such as triethylamine, may be used to neutralize the acid formed during the silylation reaction.

The amount of the carboxylic or thiocarboxylic ester containing a silylated amino group that can be added to the polymerization mixture to yield the functionalized polymer of this invention may depend on various factors including the type and amount of catalyst used to synthesize the reactive polymer and the desired degree of functionalization. In one or more embodiments, the amount of the carboxylic or thiocarboxylic ester containing a silylated amino group employed can be described with reference to the amount of the metal cation associated with the initiator. For example, where an organolithium initiator is employed, the molar ratio of the carboxylic or thiocarboxylic ester containing a silylated amino group to the lithium cation may be from about 0.3:1 to about 2:1, in other embodiments from about 0.6:1 to about 1.5:1, and in other embodiments from 0.8:1 to about 1.2:1.

In one or more embodiments, in addition to the carboxylic or thiocarboxylic ester containing a silylated amino group, a co-functionalizing agent may also be added to the polymerization mixture to yield a functionalized polymer with tailored properties. A mixture of two or more co-functionalizing agents may also be employed. The co-functionalizing agent may be added to the polymerization mixture prior to, together with, or after the introduction of the carboxylic or thiocarboxylic ester containing a silylated amino group. In one or more embodiments, the co-functionalizing agent is added to the polymerization mixture at least 5 minutes after, in other embodiments at least 10 minutes after, and in other embodiments at least 30 minutes after the introduction of the carboxylic or thiocarboxylic ester containing a silylated amino group.

In one or more embodiments, co-functionalizing agents include compounds or reagents that can react with a reactive polymer produced by this invention and thereby provide the polymer with a functional group that is distinct from a propagating chain that has not been reacted with the co-functionalizing agent. The functional group may be reactive or interactive with other polymer chains (propagating and/or non-propagating) or with other constituents such as reinforcing fillers (e.g. carbon black) that may be combined with the polymer. In one or more embodiments, the reaction between the co-functionalizing agent and the reactive polymer proceeds via an addition or substitution reaction.

Useful co-functionalizing agents may include compounds that simply provide a functional group at the end of a polymer chain without joining two or more polymer chains together, as well as compounds that can couple or join two or more polymer chains together via a functional linkage to form a single macromolecule. The latter type of co-functionalizing agents may also be referred to as coupling agents.

In one or more embodiments, co-functionalizing agents include compounds that will add or impart a heteroatom to the polymer chain. In particular embodiments, co-functionalizing agents include those compounds that will impart a functional group to the polymer chain to form a functionalized polymer that reduces the 50° C. hysteresis loss of a carbon-black filled vulcanizates prepared from the functionalized polymer as compared to similar carbon-black filled vulcanizates prepared from non-functionalized polymer. In one or more embodiments, this reduction in hysteresis loss is at least 5%, in other embodiments at least 10%, and in other embodiments at least 15%.

In one or more embodiments, suitable co-functionalizing agents include those compounds that contain groups that may react with the reactive polymers produced in accordance with this invention. Exemplary co-functionalizing agents include ketones, quinones, aldehydes, amides, esters, isocyanates, isothiocyanates, epoxides, imines, aminoketones, aminothioketones, and acid anhydrides. Examples of these compounds are disclosed in U.S. Pat. Nos. 4,906,706, 4,990,573, 5,064,910, 5,567,784, 5,844,050, 6,838,526, 6,977,281, and 6,992,147; U.S. Pat. Publication Nos. 2006/0004131 A1, 2006/0025539 A1, 2006/0030677 A1, and 2004/0147694 A1; Japanese Patent Application Nos. 05-051406A, 05-059103A, 10-306113A, and 11-035633A; which are incorporated herein by reference. Other examples of co-functionalizing agents include azine compounds as described in U.S. Ser. No. 11/640,711, hydrobenzamide compounds as disclosed in U.S. Ser. No. 11/710,713, nitro compounds as disclosed in U.S. Ser. No. 11/710,845, and protected oxime compounds as disclosed in U.S. Ser. No. 60/875,484, all of which are incorporated herein by reference.

In particular embodiments, the co-functionalizing agents employed may be metal halides, metalloid halides, alkoxysilanes, metal carboxylates, hydrocarbylmetal carboxylates, hydrocarbylmetal ester-carboxylates, and metal alkoxides.

Exemplary metal halide compounds include tin tetrachloride, tin tetrabromide, tin tetraiodide, n-butyltin trichloride, phenyltin trichloride, di-n-butyltin dichloride, diphenyltin dichloride, tri-n-butyltin chloride, triphenyltin chloride, germanium tetrachloride, germanium tetrabromide, germanium tetraiodide, n-butylgermanium trichloride, di-n-butylgermanium dichloride, and tri-n-butylgermanium chloride.

Exemplary metalloid halide compounds include silicon tetrachloride, silicon tetrabromide, silicon tetraiodide, methyltrichlorosilane, phenyltrichlorosilane, dimethyldichlorosilane, diphenyldichlorosilane, boron trichloride, boron tribromide, boron triiodide, phosphorous trichloride, phosphorous tribromide, and phosphorus triiodide.

In one or more embodiments, the alkoxysilanes may include at least one group selected from the group consisting of an epoxy group and an isocyanate group.

Exemplary alkoxysilane compounds including an epoxy group include (3-glycidyloxypropyl)trimethoxysilane, (3-glycidyloxypropyl)triethoxysilane, (3-glycidyloxypropyl)triphenoxysilane, (3-glycidyloxypropyl)methyldimethoxysilane, (3-glycidyloxypropyl)methyldiethoxysilane, (3-glycidyloxypropyl)methyldiphenoxysilane, [2-(3,4-epoxycyclohexyl)ethyl]trimethoxysilane, and [2-(3,4-epoxycyclohexyl)ethyl]triethoxysilane.

Exemplary alkoxysilane compounds including an isocyanate group include (3-isocyanatopropyl)trimethoxysilane, (3-isocyanatopropyl)triethoxysilane, (3-isocyanatopropyl)triphenoxysilane, (3-isocyanatopropyl)methyldimethoxysilane, (3-isocyanatopropyl)methyldiethoxysilane (3-isocyanatopropyl)methyldiphenoxysilane, and (isocyanatomethyl)methyldimethoxysilane.

Exemplary metal carboxylate compounds include tin tetraacetate, tin bis(2-ethylhexanaote), and tin bis(neodecanoate).

Exemplary hydrocarbylmetal carboxylate compounds include triphenyltin 2-ethylhexanoate, tri-n-butyltin 2-ethylhexanoate, tri-n-butyltin neodecanoate, triisobutyltin 2-ethylhexanoate, diphenyltin bis(2-ethylhexanoate), di-n-butyltin bis(2-ethylhexanoate), di-n-butyltin bis(neodecanoate), phenyltin tris(2-ethylhexanoate), and n-butylltin tris(2-ethylhexanoate).

Exemplary hydrocarbylmetal ester-carboxylate compounds include di-n-butyltin bis(n-octylmaleate), di-n-octyltin bis(n-octylmaleate), diphenyltin bis(n-octylmaleate), di-n-butyltin bis(2-ethylhexylmaleate), di-n-octyltin bis(2-ethylhexylmaleate), and diphenyltin bis(2-ethylhexylmaleate).

Exemplary metal alkoxide compounds include dimethoxytin, diethoxytin, tetraethoxytin, tetra-n-propoxytin, tetraisopropoxytin, tetra-n-butoxytin, tetraisobutoxytin, tetra-t-butoxytin, and tetraphenoxytin.

The amount of the co-functionalizing agent that can be added to the polymerization mixture may depend on various factors including the type and amount of initiator used to synthesize the reactive polymer and the desired degree of functionalization. In one or more embodiments, the amount of the carboxylic or thiocarboxylic ester containing a silylated amino group employed can be described with reference to the amount of metal cation associated with the initiator. For example, where an organolithium initiator is employed, the molar ratio of the carboxylic or thiocarboxylic ester containing a silylated amino group to the lithium cation may be from about 0.3:1 to about 2:1, in other embodiments from about 0.6:1 to about 1.5:1, and in other embodiments from 0.8:1 to about 1.2:1.

The amount of the co-functionalizing agent employed can also be described with reference to the carboxylic or thiocarboxylic ester containing a silylated amino group. In one or more embodiments, the molar ratio of the co-functionalizing agent to the carboxylic or thiocarboxylic ester containing a silylated amino group may be from about 0.05:1 to about 1:1, in other embodiments from about 0.1:1 to about 0.8:1, and in other embodiments from about 0.2:1 to about 0.6:1.

In one or more embodiments, the carboxylic or thiocarboxylic ester containing a silylated amino group (and optionally the co-functionalizing agent) may be introduced to the polymerization mixture at a location (e.g., within a vessel) where the polymerization has been conducted. In other embodiments, the carboxylic or thiocarboxylic ester containing a silylated amino group may be introduced to the polymerization mixture at a location that is distinct from where the polymerization has taken place. For example, the carboxylic or thiocarboxylic ester containing a silylated amino group may be introduced to the polymerization mixture in downstream vessels including downstream reactors or tanks, in-line reactors or mixers, extruders, or devolatilizers.

In one or more embodiments, the carboxylic or thiocarboxylic ester containing a silylated amino group (and optionally the co-functionalizing agent) can be reacted with the reactive polymer after a desired monomer conversion is achieved but before the polymerization mixture is quenched by a quenching agent. In one or more embodiments, the reaction between the carboxylic or thiocarboxylic ester containing a silylated amino group and the reactive polymer may take place within 30 minutes, in other embodiments within 5 minutes, and in other embodiments within one minute after the peak polymerization temperature is reached. In one or more embodiments, the reaction between the carboxylic or thiocarboxylic ester containing a silylated amino group and the reactive polymer can occur once the peak polymerization temperature is reached. In other embodiments, the reaction between the carboxylic or thiocarboxylic ester containing a silylated amino group and the reactive polymer can occur after the reactive polymer has been stored. In one or more embodiments, the storage of the reactive polymer occurs at room temperature or below room temperature under an inert atmosphere. In one or more embodiments, the reaction between the carboxylic or thiocarboxylic ester containing a silylated amino group and the reactive polymer may take place at a temperature from about 10° C. to about 150° C., and in other embodiments from about 20° C. to about 100° C. The time required for completing the reaction between the carboxylic or thiocarboxylic ester containing a silylated amino group and the reactive polymer depends on various factors such as the type and amount of the initiator used to prepare the reactive polymer, the type and amount of the carboxylic or thiocarboxylic ester containing a silylated amino group, as well as the temperature at which the functionalization reaction is conducted. In one or more embodiments, the reaction between the carboxylic or thiocarboxylic ester containing a silylated amino group and the reactive polymer can be conducted for about 10 to 60 minutes.

In one or more embodiments, after the reaction between the reactive polymer and the carboxylic or thiocarboxylic ester containing a silylated amino group (and optionally the co-functionalizing agent) has been accomplished or completed, a quenching agent can be added to the polymerization mixture in order to protonate the reaction product between the reactive polymer and the carboxylic or thiocarboxylic ester containing a silylated amino group, inactivate any residual reactive polymer chains, and/or inactivate the initiator. The quenching agent may include a protic compound, which includes, but is not limited to, an alcohol, a carboxylic acid, an inorganic acid, water, or a mixture thereof. An antioxidant such as 2,6-di-tert-butyl-4-methylphenol may be added along with, before, or after the addition of the quenching agent. The amount of the antioxidant employed may be in the range of 0.2% to 1% by weight of the polymer product. Additionally, the polymer product can be oil extended by adding an oil to the polymer, which may be in the form of a polymer cement or polymer dissolved or suspended in monomer. Practice of the present invention does not limit the amount of oil that may be added, and therefore conventional amounts may be added (e.g., 5-50 phr). Useful oils or extenders that may be employed include, but are not limited to, aromatic oils, paraffinic oils, naphthenic oils, vegetable oils other than castor oils, low PCA oils including MES, TDAE, and SRAE, and heavy naphthenic oils.

Once the polymerization mixture has been quenched, the various constituents of the polymerization mixture may be recovered. In one or more embodiments, the unreacted monomer can be recovered from the polymerization mixture. For example, the monomer can be distilled from the polymerization mixture by using techniques known in the art. In one or more embodiments, a devolatilizer may be employed to remove the monomer from the polymerization mixture. Once the monomer has been removed from the polymerization mixture, the monomer may be purified, stored, and/or recycled back to the polymerization process.

The polymer product may be recovered from the polymerization mixture by using techniques known in the art. In one or more embodiments, desolventization and drying techniques may be used. For instance, the polymer can be recovered by passing the polymerization mixture through a heated screw apparatus, such as a desolventizing extruder, in which the volatile substances are removed by evaporation at appropriate temperatures (e.g., about 100° C. to about 170° C.) and under atmospheric or sub-atmospheric pressure. This treatment serves to remove unreacted monomer as well as any low-boiling solvent. Alternatively, the polymer can also be recovered by subjecting the polymerization mixture to steam desolventization, followed by drying the resulting polymer crumbs in a hot air tunnel. The polymer can also be recovered by directly drying the polymerization mixture on a drum dryer.

While the reactive polymer and the carboxylic or thiocarboxylic ester containing a silylated amino group (and optionally the co-functionalizing agent) are believed to react to produce a novel functionalized polymer, which can be protonated or further modified, wherein the residue of the ester compound is imparted to the end of the polymer chain, which is where the reactive end of the polymer is believed to react with the ester compound. Nonetheless, the exact chemical structure of the functionalized polymer produced in every embodiment is not known with any great degree of certainty, particularly as the structure relates to the residue imparted to the polymer chain end by the carboxylic or thiocarboxylic ester containing a silylated amino group and optionally the co-functionalizing agent. Indeed, it is speculated that the structure of the functionalized polymer may depend upon various factors such as the conditions employed to prepare the reactive polymer (e.g., the type and amount of the initiator) and the conditions employed to react the carboxylic or thiocarboxylic ester containing a silylated amino group (and optionally the co-functionalizing agent) with the reactive polymer (e.g., the types and amounts of the carboxylic or thiocarboxylic ester containing a silylated amino group and the co-functionalizing agent).

In one or more embodiments, the functionalized polymers prepared according to this invention may contain unsaturation. In these or other embodiments, the functionalized polymers are vulcanizable. In one or more embodiments, the functionalized polymers can have a glass transition temperature ($T_g$) that is less than 0° C., in other embodiments less than −20° C., and in other embodiments less than −30° C. In one embodiment, these polymers may exhibit a single glass transition temperature. In particular embodiments, the polymers may be hydrogenated or partially hydrogenated.

The number average molecular weight ($M_n$) of the functionalized polymers prepared according to this invention may be from about 1,000 to about 1,000,000, in other embodiments from about 5,000 to about 1,000,000, in other embodiments from about 50,000 to about 500,000, and in other embodiments from about 100,000 to about 300,000, as determined by using gel permeation chromatography (GPC) calibrated with polystyrene standards and Mark-Houwink constants for the polymer in question. The molecular weight distribution or polydispersity ($M_w/M_n$) of these polymers may be from about 1.0 to about 3.0, and in other embodiments from about 1.1 to about 2.0.

In one or more embodiments, the functionalized polymers of this invention may be polydienes or copolymers of conjugated diene and co-monomer having medium or low cis-1,4-linkage contents. These polymers can have a cis-1,4-linkage content of from about 10% to 60%, in other embodiments from about 15% to 55%, and in other embodiments from about 20% to about 50%. These polymers may also have a 1,2-linkage content from about 10% to about 90%, in other embodiments from about 10% to about 60%, in other embodiments from about 15% to about 50%, and in other embodiments from about 20% to about 45%. In particular embodiments, where the polymers are prepared by employing a functional anionic initiator, the head of the polymer chain includes a functional group that is the residue of the functional initiator.

In one or more embodiments, the functionalized polymer of this invention is a polymer selected from the group consisting of polybutadiene, polyisoprene, poly(styrene-co-butadiene), poly(styrene-co-butadiene-co-isoprene), poly(isoprene-co-styrene), and poly(butadiene-co-isoprene).

In particular embodiments, the functionalized polymers of this invention are copolymers of 1,3-butadiene, styrene, and optionally isoprene. These copolymer may include random copolymers and block copolymers.

Advantageously, the functionalized polymers of this invention may provide rubber compositions that demonstrate reduced hysteresis. The functionalized polymers are particularly useful in preparing rubber compositions that can be used to manufacture tire components. Rubber compounding techniques and the additives employed therein are generally disclosed in *The Compounding and Vulcanization of Rubber*, in *Rubber Technology* (2nd Ed. 1973).

The rubber compositions can be prepared by using the functionalized polymers alone or together with other elastomers (i.e., polymers that can be vulcanized to form compositions possessing rubbery or elastomeric properties). Other elastomers that may be used include natural and synthetic rubbers. The synthetic rubbers typically derive from the polymerization of conjugated diene monomers, the copolymerization of conjugated diene monomers with other monomers such as vinyl-substituted aromatic monomers, or the copolymerization of ethylene with one or more α-olefins and optionally one or more diene monomers.

Exemplary elastomers include natural rubber, synthetic polyisoprene, polybutadiene, polyisobutylene-co-isoprene, neoprene, poly(ethylene-co-propylene), poly(styrene-co-butadiene), poly(styrene-co-isoprene), poly(styrene-co-isoprene-co-butadiene), poly(isoprene-co-butadiene), poly(ethylene-co-propylene-co-diene), polysulfide rubber, acrylic rubber, urethane rubber, silicone rubber, epichlorohydrin rubber, and mixtures thereof. These elastomers can have a myriad of macromolecular structures including linear, branched, and star-shaped structures.

The rubber compositions may include fillers such as inorganic and organic fillers. Examples of organic fillers include carbon black and starch. Examples of inorganic fillers include silica, aluminum hydroxide, magnesium hydroxide, mica, talc (hydrated magnesium silicate), and clays (hydrated aluminum silicates). Carbon blacks and silicas are the most common fillers used in manufacturing tires. In certain embodiments, a mixture of different fillers may be advantageously employed.

In one or more embodiments, carbon blacks include furnace blacks, channel blacks, and lamp blacks. More specific examples of carbon blacks include super abrasion furnace blacks, intermediate super abrasion furnace blacks, high abrasion furnace blacks, fast extrusion furnace blacks, fine furnace blacks, semi-reinforcing furnace blacks, medium processing channel blacks, hard processing channel blacks, conducting channel blacks, and acetylene blacks.

In particular embodiments, the carbon blacks may have a surface area (EMSA) of at least 20 m$^2$/g and in other embodiments at least 35 m$^2$/g; surface area values can be determined by ASTM D-1765 using the cetyltrimethylammonium bromide (CTAB) technique. The carbon blacks may be in a pelletized form or an unpelletized flocculent form. The preferred form of carbon black may depend upon the type of mixing equipment used to mix the rubber compound.

The amount of carbon black employed in the rubber compositions can be up to about 50 parts by weight per 100 parts by weight of rubber (phr), with about 5 to about 40 phr being typical.

Some commercially available silicas which may be used include Hi-Sil™ 215, Hi-Sil™ 233, and Hi-Sil™ 190 (PPG Industries, Inc.; Pittsburgh, Pa.). Other suppliers of commercially available silica include Grace Davison (Baltimore, Md.), Degussa Corp. (Parsippany, N.J.), Rhodia Silica Systems (Cranbury, N.J.), and J.M. Huber Corp. (Edison, N.J.).

In one or more embodiments, silicas may be characterized by their surface areas, which give a measure of their reinforcing character. The Brunauer, Emmet and Teller ("BET") method (described in *J. Am. Chem. Soc.*, vol. 60, p. 309 et seq.) is a recognized method for determining the surface area. The BET surface area of silica is generally less than 450 m$^2$/g. Useful ranges of surface area include from about 32 to about 400 m$^2$/g, about 100 to about 250 m$^2$/g, and about 150 to about 220 m$^2$/g.

The pH's of the silicas are generally from about 5 to about 7 or slightly over 7, or in other embodiments from about 5.5 to about 6.8.

In one or more embodiments, where silica is employed as a filler (alone or in combination with other fillers), a coupling agent and/or a shielding agent may be added to the rubber compositions during mixing in order to enhance the interaction of silica with the elastomers. Useful coupling agents and shielding agents are disclosed in U.S. Pat. Nos. 3,842,111, 3,873,489, 3,978,103, 3,997,581, 4,002,594, 5,580,919, 5,583,245, 5,663,396, 5,674,932, 5,684,171, 5,684,172 5,696,197, 6,608,145, 6,667,362, 6,579,949, 6,590,017, 6,525,118, 6,342,552, and 6,683,135, which are incorporated herein by reference.

The amount of silica employed in the rubber compositions can be from about 1 to about 100 phr or in other embodiments from about 5 to about 80 phr. The useful upper range is limited by the high viscosity imparted by silicas. When silica is used together with carbon black, the amount of silica can be decreased to as low as about 1 phr; as the amount of silica is decreased, lesser amounts of coupling agents and shielding agents can be employed. Generally, the amounts of coupling agents and shielding agents range from about 4% to about 20% based on the weight of silica used.

A multitude of rubber curing agents (also called vulcanizing agents) may be employed, including sulfur or peroxide-based curing systems. Curing agents are described in Kirk-Othmer, ENCYCLOPEDIA OF CHEMICAL TECHNOLOGY, Vol. 20, pgs. 365-468, (3$^{rd}$ Ed. 1982), particularly *Vulcanization Agents and Auxiliary Materials*, pgs. 390-402, and A. Y. Coran, *Vulcanization*, ENCYCLOPEDIA OF POLYMER SCIENCE AND ENGINEERING, (2$^{nd}$ Ed. 1989), which are incorporated herein by reference. Vulcanizing agents may be used alone or in combination.

Other ingredients that are typically employed in rubber compounding may also be added to the rubber compositions. These include accelerators, accelerator activators, oils, plasticizer, waxes, scorch inhibiting agents, processing aids, zinc oxide, tackifying resins, reinforcing resins, fatty acids such as stearic acid, peptizers, and antidegradants such as antioxidants and antiozonants. In particular embodiments, the oils that are employed include those conventionally used as extender oils, which are described above.

All ingredients of the rubber compositions can be mixed with standard mixing equipment such as Banbury or Brabender mixers, extruders, kneaders, and two-rolled mills. In one or more embodiments, the ingredients are mixed in two or more stages. In the first stage (often referred to as the masterbatch mixing stage), a so-called masterbatch, which typically includes the rubber component and filler, is prepared. To prevent premature vulcanization (also known as scorch), the masterbatch may exclude vulcanizing agents. The masterbatch may be mixed at a starting temperature of from about 25° C. to about 125° C. with a discharge temperature of about 135° C. to about 180° C. Once the masterbatch is prepared, the vulcanizing agents may be introduced and mixed into the masterbatch in a final mixing stage, which is typically conducted at relatively low temperatures so as to reduce the chances of premature vulcanization. Optionally, additional mixing stages, sometimes called remills, can be employed between the masterbatch mixing stage and the final mixing stage. One or more remill stages are often employed where the rubber composition includes silica as the filler. Various ingredients including the functionalized polymers of this invention can be added during these remills.

The mixing procedures and conditions particularly applicable to silica-filled tire formulations are described in U.S. Pat. Nos. 5,227,425, 5,719,207, and 5,717,022, as well as European Patent No. 890,606, all of which are incorporated herein by reference. In one embodiment, the initial masterbatch is prepared by including the functionalized polymer of this invention and silica in the substantial absence of coupling agents and shielding agents.

The rubber compositions prepared from the functionalized polymers of this invention are particularly useful for forming tire components such as treads, subtreads, sidewalls, body ply skims, bead filler, and the like. Preferably, the functional polymers of this invention are employed in tread and sidewall formulations. In one or more embodiments, these tread or sidewall formulations may include from about 10% to about 100% by weight, in other embodiments from about 35% to about 90% by weight, and in other embodiments from about 50% to about 80% by weight of the functionalized polymer based on the total weight of the rubber within the formulation.

Where the rubber compositions are employed in the manufacture of tires, these compositions can be processed into tire components according to ordinary tire manufacturing techniques including standard rubber shaping, molding and curing techniques. Typically, vulcanization is effected by heating the vulcanizable composition in a mold; e.g., it may be heated to about 140° C. to about 180° C. Cured or crosslinked rubber compositions may be referred to as vulcanizates, which generally contain three-dimensional polymeric networks that are thermoset. The other ingredients, such as fillers and processing aids, may be evenly dispersed throughout the crosslinked network. Pneumatic tires can be made as discussed in U.S. Pat. Nos. 5,866,171, 5,876,527, 5,931,211, and 5,971,046, which are incorporated herein by reference.

In order to demonstrate the practice of the present invention, the following examples have been prepared and tested. The examples should not, however, be viewed as limiting the scope of the invention. The claims will serve to define the invention.

EXAMPLES

Example 1

Synthesis of Ethyl
3-[Bis(trimethylsilyl)amino]propionate
(3-BTMSAEP)

About 7.23 g of ethyl 3-aminopropionate hydrochloride, 15.71 g of triethylamine, and 10 ml of toluene were mixed in a round-bottom reaction flask cooled with an ice bath. To this mixture was added, in a dropwise fashion, a solution of 23.00 g of trimethylsilyl trifluoromethanesulfonate in 50 ml of toluene. The resulting mixture was stirred at room temperature for 39 hours to give a biphasic mixture. The top layer was transferred to another flask, and the bottom layer was extracted with 40 ml of toluene. The combined toluene solution was evaporated under vacuum. The residue was extracted with 100 ml of hexane, and the hexane layer was evaporated under vacuum, yielding ethyl 3-[bis(trimethylsilyl)amino] propionate (3-BTMSAEP) as a colorless oil (11.03 g, 90% yield). The $^1$H NMR data ($C_6D_6$, 25° C., referenced to tetramethylsilane) of the product are listed as follows: δ 3.91 (quartet, 2H, $OCH_2$ protons), 3.21 (multiplet, 2H, $NCH_2CH_2$ protons), 2.36 (multiplet, 2H, $NCH_2CH_2$ protons), 0.91 (triplet, 3H, $CH_3$ protons), 0.07 (singlet, 18H, Si—$CH_3$ protons). From the $^1$H NMR data, the structure of the product was determined to be as follows:

3-BTMSAEP

Example 2

Synthesis of Ethyl
4-[Bis(trimethylsilyl)amino]benzoate
(4-BTMSAEBz)

About 9.24 g of ethyl 4-aminobenzoate, 14.88 g of triethylamine, and 10 ml of toluene were mixed in a round-bottom reaction flask cooled with an ice bath. To this mixture was added, in a dropwise fashion, a solution of 32.68 g of trimethylsilyl trifluoromethanesulfonate in 50 ml of toluene. The resulting mixture was heated to reflux for 8 hours to give a biphasic mixture. The top layer was transferred to another flask, and the bottom layer was extracted with 40 ml of toluene. The combined toluene solution was evaporated under vacuum. The residue was extracted with 100 ml of hexane, and the hexane layer was evaporated under vacuum, yielding ethyl 4-[bis(trimethylsilyl)amino]benzoate (4-BTMSAEBz) as a yellow oil (16.04 g, 93% yield). The $^1$H NMR data ($C_6D_6$, 25° C., referenced to tetramethylsilane) of the product are listed as follows: δ 8.07 (doublet, 2H, aromatic protons), 6.76 (doublet, 2H, aromatic protons), 4.12 (quartet, 2H, $CH_2$ protons), 1.00 (triplet, 3H, $CH_3$ protons), 0.02 (singlet, 18H, Si—$CH_3$ protons). From the $^1$H NMR data, the structure of the product was determined to be as follows:

4-BTMSAEBz

Example 3

Synthesis of Unmodified Poly(styrene-co-butadiene)

To a 5-gallon nitrogen-purged reactor equipped with turbine agitator blades were added 5100 g of hexane, 1278 g of 33.0 wt % styrene in hexane, and 7670 g of 22.0 wt % 1,3-butadiene in hexane. To the reactor were charged 11.98 ml of 1.6 M n-butyllithium in hexane and 3.95 ml of 1.6 M 2,2-bis(2'-tetrahydrofuryl)propane in hexane. The batch was heated by applying hot water to the reactor jacket. Once the batch temperature reached 50° C., the reactor jacket was cooled with cold water.

Ninety minutes after the addition of the catalyst, about 420 g of the resulting living polymer cement was transferred from the reactor into a nitrogen-purged bottle and quenched by addition of 3 ml of 12 wt % 2,6-di-tert-butyl-4-methylphenol solution in isopropanol. The resulting mixture was coagulated with 2 liters of isopropanol containing 0.5 g of 2,6-di-tert-butyl-4-methylphenol and then drum-dried.

The Mooney viscosity ($ML_{1+4}$) of the resulting polymer was determined to be 13.6 at 100° C. by using an Alpha Technologies Mooney viscometer with a large rotor, a one-minute warm-up time, and a four-minute running time. As determined by gel permeation chromatography (GPC), the polymer had a number average molecular weight ($M_n$) of 116,600, a weight average molecular weight ($M_w$) of 120, 200, and a molecular weight distribution ($M_w/M_n$) of 1.03. The $^1$H NMR analysis of the polymer indicated that the polymer had a styrene content of 20.7 wt % and a 1,2-linkage (based on butadiene mer units) of 55.5%. The properties of the resulting unmodified poly(styrene-co-butadiene) are summarized in Table 1.

TABLE 1

Physical Properties of Poly(styrene-co-butadiene)

| | Example No. | | | |
|---|---|---|---|---|
| | Example 3 | Example 4 | Example 5 | Example 6 (Comparative) |
| Polymer type | unmodified | unmodified | 3-BTMSAEP-modified | 4-BTMSAEBz-modified |
| $ML_{1+4}$ at 100° C. | 13.6 | 97.2 | 46.9 | 54.6 |

TABLE 1-continued

Physical Properties of Poly(styrene-co-butadiene)

| | Example No. | | | |
|---|---|---|---|---|
| | Example 3 | Example 4 | Example 5 | Example 6 (Comparative) |
| $M_n$ | 116,600 | 257,500 | 156,700 | 171,600 |
| $M_w$ | 120,200 | 282,100 | 197,900 | 199,900 |
| $M_w/M_n$ | 1.03 | 1.10 | 1.26 | 1.17 |
| % styrene | 20.7 | 20.0 | 20.7 | 20.7 |
| % 1,2 | 55.5 | 55.9 | 55.5 | 55.5 |

Example 4

Synthesis of Unmodified Poly(Styrene-Co-Butadiene)

To a 2-gallon nitrogen-purged reactor equipped with turbine agitator blades was added 1595 g of hexane, 400 g of 34.0 wt % styrene in hexane, and 2440 g of 22.3 wt % 1,3-butadiene in hexane. To the reactor was charged 1.70 ml of 1.6 M n-butyllithium in hexane and 0.56 mL of 1.6 M 2,2-bis(2'-tetrahydrofuryl)propane in hexane. The batch was heated by applying hot water to the reactor jacket. Once the batch temperature reached 50° C., the reactor jacket was cooled with cold water. About 2.5 hours after the addition of the catalyst, the polymerization mixture was quenched with 30 ml of 12 wt % 2,6-di-tert-butyl-4-methylphenol solution in isopropanol, coagulated with 12 liters of isopropanol containing 5 g of 2,6-di-tert-butyl-4-methylphenol, and then drum-dried. The properties of the resulting unmodified SBR are summarized in Table 1.

Example 5

Synthesis of Poly(Styrene-Co-Butadiene) Modified with Ethyl 3-[Bis(trimethylsilyl)amino]propionate (3-BTMSAEP)

About 343 g of the living polymer cement as synthesized in Example 3 was transferred from the reactor to a nitrogen-purged bottle, followed by addition of 0.95 ml of 0.45 M ethyl 3-[bis(trimethylsilyl)amino]propionate (3-BTMSAEP) in hexane. The bottle was tumbled for 30 minutes in a water bath maintained at 65° C. The resulting polymer cement was quenched with 3 ml of 12 wt % 2,6-di-tert-butyl-4-methylphenol solution in isopropanol, coagulated with 2 liters of isopropanol containing 0.5 g of 2,6-di-tert-butyl-4-methylphenol, and then drum-dried. The properties of the resulting 3-BTMSAEP-modified polymer are summarized in Table 1.

Example 6 (Comparative Example)

Synthesis of Poly(styrene-co-butadiene) Modified with Ethyl 4-[Bis(trimethylsilyl)amino]benzoate (4-BTMSAEBz)

About 335 g of the living polymer cement as synthesized in Example 3 was transferred from the reactor to a nitrogen-purged bottle, followed by addition of 0.93 ml of 0.45 M ethyl 4-[bis(trimethylsilyl)amino]benzoate (4-BTMSAEBz) in hexane. The bottle was tumbled for 30 minutes in a water bath maintained at 65° C. The resulting polymer cement was quenched with 3 ml of 12 wt % 2,6-di-tert-butyl-4-methylphenol solution in isopropanol, coagulated with 2 liters of isopropanol containing 0.5 g of 2,6-di-tert-butyl-4-methylphenol, and then drum-dried. The properties of the resulting 4-BTMSAEBz-modified polymer are summarized in Table 1.

Examples 7-10

Compounding Evaluation of 3-BTMSAEP- and 4-BTMSAEBz-Modified Poly(Styrene-Co-Butadiene) Versus Unmodified Poly(Styrene-Co-Butadiene)

The poly(styrene-co-butadiene) samples produced in Examples 3-6 were evaluated in a rubber compound filled with carbon black. The compositions of the vulcanizates are presented in Table 2, wherein the numbers are expressed as parts by weight per hundred parts by weight of total rubber (phr).

TABLE 2

Compositions of Rubber Vulcanizates Prepared from Poly(styrene-co-butadiene)

| Ingredient | Amount (phr) |
| --- | --- |
| SBR sample | 100 |
| Carbon black | 50 |
| Oil | 10 |
| Wax | 2 |
| Antioxidant | 0.95 |
| Zinc oxide | 2.5 |
| Stearic acid | 2 |
| Accelerators | 1.3 |
| Sulfur | 1.5 |
| Total | 170.25 |

Figure 1:
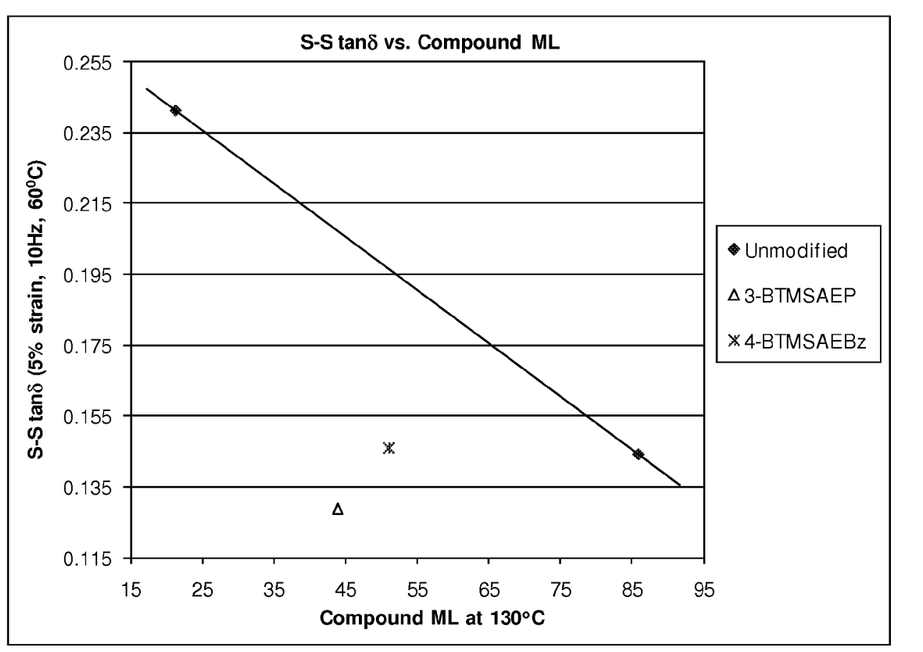
FIG. 1 is a graphical plot of hysteresis loss (tan δ) versus Mooney viscosity (ML 1+4 at 130° C.) for vulcanizates prepared from functionalized poly(styrene-co-butadiene) prepared according to one or more embodiments of the present invention as compared to vulcanizate prepared from unfunctionalized poly(styrene-co-butadiene).

The Mooney viscosity ($ML_{1+4}$) of the uncured rubber compound was determined at 130° C. by using an Alpha Technologies Mooney viscometer with a large rotor, a one-minute warm-up time, and a four-minute running time. The Payne effect data ($\Delta G'$) and hysteresis data (tan δ) of the vulcanizates were obtained from a dynamic strain-sweep experiment, which was conducted at 60° C. and 10 Hz with strain sweeping from 0.25% to 15%. $\Delta G'$ is the difference between G' at 0.25% strain and G' at 15% strain. The physical properties of the vulcanizates are summarized in Table 3. In FIG. 1, the tan δ data are plotted against the compound Mooney viscosities.

TABLE 3

Physical Properties of Rubber Vulcanizates Prepared from Poly(styrene-co-butadiene)

| | Example No. | | | |
| --- | --- | --- | --- | --- |
| | Example 7 | Example 8 | Example 9 | Example 10 (Comparative) |
| Polymer used | Example 3 | Example 4 | Example 5 | Example 6 |
| Polymer type | unmodified | unmodified | 3-BTMSAEP-modified | 4-BTMSAEBz-modified |
| Compound $ML_{1+4}$ at 130° C. | 21.4 | 86.0 | 44.0 | 51.1 |
| tan δ at 60° C., 5% strain | 0.241 | 0.144 | 0.129 | 0.146 |
| $\Delta G'$ (MPa) | 4.16 | 1.71 | 0.67 | 1.13 |

As can be seen in Table 3 and FIG. 1, the 3-BTMSAEP- and 4-BTMSAEBz-modified poly(styrene-co-butadiene) samples give lower tan δ than the unmodified polymer, indicating that the modification of poly(styrene-co-butadiene) with 3-BTMSAEP and 4-BTMSAEBz reduces hysteresis. The 3-BTMSAEP- and 4-BTMSAEBz-modified poly(styrene-co-butadiene) samples also give lower $\Delta G'$ than the unmodified polymer, indicating that the Payne Effect has been reduced due to the interaction between the modified polymer and carbon black. However, although 3-BTMSAEP and 4-BTMSAEBz contain the same bis(trimethylsilyl) amino group, the poly(styrene-co-butadiene) sample modified with 3-BTMSAEP where the bis(trimethylsilyl)amino group is directly attached to an acyclic moiety provides lower tan δ and lower $\Delta G'$ (Examples 5 and 9) as compared to the poly(styrene-co-butadiene) sample modified with 4-BTMSAEBz where the bis(trimethylsilyl)amino group is directly attached to an aromatic moiety that is devoid of heteroatoms (Examples 6 and 10 (comparative examples)).

Various modifications and alterations that do not depart from the scope and spirit of this invention will become apparent to those skilled in the art. This invention is not to be duly limited to the illustrative embodiments set forth herein.

What is claimed is:

1. A method for preparing a functionalized polymer, the method comprising the steps of:
   (i) polymerizing monomer with an anionic initiator to form a reactive polymer; and
   (ii) reacting the reactive polymer with a carboxylic or thiocarboxylic ester containing a silylated amino group, where the carboxylic or thiocarboxylic ester containing a silylated amino group is selected from the group consisting of alkenecarboxylic esters, alkynecarboxylic esters, a cycloalkenecarboxylic esters, cycloalkynecarboxylic esters, heterocyclic carboxylic esters, alkenethiocarboxylic esters, alkynethiocarboxylic esters, cycloalkenethiocarboxylic esters, cycloalkynethiocarboxylic esters, and heterocyclic thiocarboxylic esters.

2. The method of claim 1, where the silylated amino group is selected from the group consisting of bis(trihydrocarbylsilyl)amino, bis(dihydrocarbylhydrosilyl)amino, 1-aza-disila-1-cyclohydrocarbyl, (trihydrocarbylsilyl) (hydrocarbyl) amino, (dihydrocarbylhydrosilyl) (hydrocarbyl)amino, and 1-aza-2-sila-1-cyclohydrocarbyl groups.

3. The method of claim 1, where the anionic initiator is an organolithium compound and the monomer includes conjugated diene monomer and optionally monomer copolymerizable therewith.

4. The method of claim 1, where the carboxylic or thiocarboxylic ester containing a silylated amino group is an alkenecarboxylic esters containing a silylated amino group is selected from the group consisting of [bis(trihydrocarbylsilyl)amino]alkenecarboxylic esters, [bis(dihydrocarbylhydrosilyl)amino]alkenecarboxylic esters, (1-aza-disila-1-cyclohydrocarbyl)alkenecarboxylic esters, [(trihydrocarbylsilyl) (hydrocarbyl)amino]alkenecarboxylic esters, [(dihydrocarbylhydrosilyl) (hydrocarbyl)amino]alkenecarboxylic esters, and (1-aza-2-sila-1-cyclohydrocarbyl) alkenecarboxylic esters.

5. The method of claim 1, where the carboxylic or thiocarboxylic ester containing a silylated amino group is an alkynecarboxylic esters containing a silylated amino group is selected from the group consisting of [bis(trihydrocarbylsilyl)amino]alkynecarboxylic esters, [bis(dihydrocarbylhydrosilyl)amino]alkynecarboxylic esters, (1-aza-disila-1-cyclohydrocarbyl)alkynecarboxylic esters, [(trihydrocarbylsilyl) (hydrocarbyl)amino]alkynecarboxylic esters, [(dihydrocarbylhydrosilyl) (hydrocarbyl)amino]alkynecarboxylic esters, and (1-aza-2-sila-1-cyclohydrocarbyl)alkynecarboxylic esters.

6. The method of claim 1, where the carboxylic or thiocarboxylic ester containing a silylated amino group is a cycloalkenecarboxylic esters containing a silylated amino group is selected from the group consisting of [bis(trihydrocarbylsilyl)amino]cycloalkenecarboxylic esters, [bis(dihydrocarbylhydrosilyl)amino]cycloalkenecarboxylic esters, (1-aza-disila-1-cyclohydrocarbyl)cycloalkenecarboxylic esters, [(trihydrocarbylsilyl)(hydrocarbyl)amino]cycloalkenecarboxylic esters, [(dihydrocarbylhydrosilyl)(hydrocarbyl)amino]cycloalkenecarboxylic esters, and (1-aza-2-sila-1-cyclohydrocarbyl)cycloalkenecarboxylic esters.

7. The method of claim 1, where the carboxylic or thiocarboxylic ester containing a silylated amino group is a cycloalkynecarboxylic esters containing a silylated amino group is selected from the group consisting of [bis(trihydrocarbylsilyl)amino]cycloalkynecarboxylic esters, [bis(dihydrocarbylhydrosilyl)amino]cycloalkynecarboxylic esters, (1-aza-disila-1-cyclohydrocarbyl)cycloalkynecarboxylic esters, [(trihydrocarbylsilyl) (hydrocarbyl)amino]cycloalkynecarboxylic esters, [(dihydrocarbylhydrosilyl)(hydrocarbyl)amino]cycloalkynecarboxylic esters, and (1-aza-2-sila-1-cyclohydrocarbyl)cycloalkynecarboxylic esters.

8. The method of claim 1, where the carboxylic or thiocarboxylic ester containing a silylated amino group is a heterocyclic carboxylic esters containing a silylated amino group is selected from the group consisting of [bis(trihydrocarbylsilyl)amino]heterocyclic carboxylic esters, [bis(dihydrocarbylhydrosilyl)amino]heterocyclic carboxylic esters, (1-aza-disila-1-cyclohydrocarbyl) hetero cyclic carboxylic esters, [(trihydrocarbylsilyl)(hydrocarbyl)amino]heterocyclic carboxylic esters, [(dihydrocarbylhydrosilyl)(hydrocarbyl)amino]heterocyclic carboxylic esters, and (1-aza-2-sila-1-cyclohydrocarbyl)heterocyclic carboxylic esters.

9. The method of claim 1, where the carboxylic or thiocarboxylic ester containing a silylated amino group is an alkenethiocarboxylic esters containing a silylated amino group is selected from the group consisting of [bis(trihydrocarbylsilyl)amino]alkenethiocarboxylic esters, [bis(dihydrocarbylhydrosilyl)amino]alkenethiocarboxylic esters, (1-aza-disila-1-cyclohydrocarbyl)alkenethiocarboxylic esters, [(trihydrocarbylsilyl) (hydrocarbyl)amino]alkenethiocarboxylic esters, [(dihydrocarbylhydrosilyl)(hydrocarbyl)amino]alkenethiocarboxylic esters, and (1-aza-2-sila-1-cyclohydrocarbyl)alkenethiocarboxylic esters.

10. The method of claim 1, where the carboxylic or thiocarboxylic ester containing a silylated amino group is an alkynethiocarboxylic esters containing a silylated amino group is selected from the group consisting of [bis(trihydrocarbylsilyl)amino]alkynethiocarboxylic esters, [bis(dihydrocarbylhydrosilyl)amino]alkynethiocarboxylic esters, (1-aza-disila-1-cyclohydrocarbyl)alkynethiocarboxylic esters, [(trihydrocarbylsilyl) (hydrocarbyl)amino]alkynethiocarboxylic esters, [(dihydrocarbylhydrosilyl)(hydrocarbyl)amino]alkynethiocarboxylic esters, and (1-aza-2-sila-1-cyclohydrocarbyl)alkynethiocarboxylic esters.

11. The method of claim 1, where the carboxylic or thiocarboxylic ester containing a silylated amino group is a cycloalkanethiocarboxylic esters containing a silylated amino group is selected from the group consisting of [bis(trihydrocarbylsilyl)amino]cycloalkanethiocarboxylic esters, [bis(dihydrocarbylhydrosilyl)amino]cycloalkanethiocarboxylic esters, (1-aza-disila-1-cyclohydrocarbyl)cycloalkanethiocarboxylic esters, [(trihydrocarbylsilyl) (hydrocarbyl)amino]cycloalkanethiocarboxylic esters, [(dihydrocarbylhydrosilyl)(hydrocarbyl)amino]cycloalkanethiocarboxylic esters, and (1-aza-2-sila-1-cyclohydrocarbyl)cycloalkanethiocarboxylic esters.

12. The method of claim 1, where the carboxylic or thiocarboxylic ester containing a silylated amino group is a cycloalkenethiocarboxylic esters containing a silylated amino group include [bis(trihydrocarbylsilyl)amino]cycloalkenethiocarboxylic esters, [bis(dihydrocarbylhydrosilyl)amino]cycloalkenethiocarboxylic esters, (1-aza-disila-1-cyclohydrocarbyl)cycloalkenethiocarboxylic esters, [(trihydrocarbylsilyl) (hydrocarbyl)amino]cycloalkenethiocarboxylic esters, [(dihydrocarbylhydrosilyl) (hydrocarbyl)amino]cycloalkenethiocarboxylic esters, and (1-aza-2-sila-1-cyclohydrocarbyl)cycloalkenethiocarboxylic esters.

13. The method of claim 1, where the carboxylic or thiocarboxylic ester containing a silylated amino group is an heterocyclic thiocarboxylic esters containing a silylated amino group include [bis(trihydrocarbylsilyl)amino]heterocyclic thiocarboxylic esters, [bis(dihydrocarbylhydrosilyl)amino]heterocyclic thiocarboxylic esters, (1-aza-disila-1-cyclohydrocarbyl) hetero cyclic thiocarboxylic esters, [(trihydrocarbylsilyl)(hydrocarbyl)amino]heterocyclic thiocarboxylic esters, [(dihydrocarbylhydrosilyl)(hydrocarbyl)amino]heterocyclic thiocarboxylic esters, and (1-aza-2-sila-1-cyclohydrocarbyl)heterocyclic thiocarboxylic esters.

\* \* \* \* \*